United States Patent
Yu et al.

(10) Patent No.: US 10,724,099 B2
(45) Date of Patent: Jul. 28, 2020

(54) MULTIPLEX METHODS TO ASSAY MIXED CELL POPULATIONS SIMULTANEOUSLY

(71) Applicants: The Broad Institute, Inc., Cambridge, MA (US); Dana Farber Cancer Institute, Inc., Boston, MA (US)

(72) Inventors: Channing Yu, Cambridge, MA (US); Todd R. Golub, Newton, MA (US)

(73) Assignees: The Broad Institute, Inc., Cambridge, MA (US); Dana Farber Cancer Institute, Inc., Boston, MA (US)

( * ) Notice: Subject to any disclaimer, the term of this patent is extended or adjusted under 35 U.S.C. 154(b) by 342 days.

(21) Appl. No.: 14/385,545

(22) PCT Filed: Mar. 14, 2013

(86) PCT No.: PCT/US2013/031312
§ 371 (c)(1),
(2) Date: Sep. 16, 2014

(87) PCT Pub. No.: WO2013/138585
PCT Pub. Date: Sep. 19, 2013

(65) Prior Publication Data
US 2015/0044676 A1    Feb. 12, 2015

Related U.S. Application Data

(60) Provisional application No. 61/612,013, filed on Mar. 16, 2012.

(51) Int. Cl.
| | | |
|---|---|---|
| C12P 19/34 | (2006.01) |
| C12Q 1/6886 | (2018.01) |
| G01N 33/50 | (2006.01) |
| C12Q 1/686 | (2018.01) |

(52) U.S. Cl.
CPC .......... *C12Q 1/6886* (2013.01); *C12Q 1/686* (2013.01); *G01N 33/5041* (2013.01); *C12Q 2600/112* (2013.01)

(58) Field of Classification Search
None
See application file for complete search history.

(56) References Cited

U.S. PATENT DOCUMENTS

| | | | |
|---|---|---|---|
| 5,068,178 A | 11/1991 | Nowinski | |
| 2003/0033627 A1* | 2/2003 | Descenzo | C12N 9/0069 800/278 |
| 2005/0009060 A1 | 1/2005 | Beernink et al. | |
| 2009/0088341 A1 | 4/2009 | Zudaire et al. | |
| 2011/0190163 A1* | 8/2011 | Hoe | C12N 15/1034 506/10 |
| 2013/0236568 A1* | 9/2013 | Bose | A61K 31/282 424/649 |

FOREIGN PATENT DOCUMENTS

| | | |
|---|---|---|
| EP | 0470810 | 2/1992 |
| WO | WO 2003/006947 | 1/2003 |
| WO | WO 2012/130720 | 10/2012 |

OTHER PUBLICATIONS

Yu et al., High-throughput identification of genotype-specific cancer vulnerabilities in mixtures of barcoded tumor cell lines. Nature Biotechnology, 34, 419-423, 2016.*
Delneri, Barcode technology in yeast: application to pharmacogenomics. FEMS Yeast Res., 10, 1083-1089, 2010.*
International Search Report and Written Opinion in International Application No. PCT/US2013/031312, dated Jul. 9, 2013, 10 pages.
International Preliminary Report on Patentability in International Application No. PCT/US2013/031312, dated Sep. 16, 2014, 7 pages.
Andrews et al., "Mitotic mechanics: the auroras come into view," Curr Opin Cell Biol., 15:672-683 (Dec. 2003).
Barretina et al., "The Cancer Cell Line Encyclopedia enables predictive modelling of anticancer drug sensitivity," Nature 483(7391):603-607 (Mar. 29, 2012) (Author Manuscript).
Berns et al., "A large-scale RNAi screen in human cells identifies new components of the p53 pathway," Nature 428:431-437 (Mar. 2004).
Broad Institute, "Program and Abstracts, The Second East Coast Academic Screening Symposium" (Sep. 28, 2011) Retrieved on Jan. 12, 2015. Retrieved from the Internet: https://www.broadinstitute.org/scientific-community/science/platforms/therapeutics-platform/screening-symposium/program-and-abs, 4 pages.
Carmena and Earnshaw, "The cellular geography of aurora kinases," Nat Rev Mol Cell Biol., 4:842-54 (Nov. 2003).
Comer et al., "Fragment-based domain shuffling approach for the synthesis of pyran-based macrocycles," Proc Natl Acad Sci USA, 108(17):6751-6 (Apr. 26, 2011).
Craig et al., "Identification of genetic variants using bar-coded multiplexed sequencing," Nat. Methods, 5(10):887-893 (Oct. 2008) (Author Manuscript).
Ditchfield et al., "Aurora B couples chromosome alignment with anaphase by targeting BubR1, Mad2, and Cenp-E to kinetochores," J Cell Biol., 161:267-80 (Apr. 28, 2003).
Garnett et al., "Systematic identification of genomic markers of drug sensitivity in cancer cells," Nature, 483:570-5 (Mar. 29, 2012) (Author Manuscript).
Gerrits et al., "Cellular barcoding tool for clonal analysis in the hematopoietic system," Blood, 115:2610-2618 (Apr. 2010).
Koivunen et al., "EML4-ALK Fusion Gene and Efficacy of an ALK Kinase Inhibitor in Lung Cancer," Clin Cancer Res 14(13):4275-4283 (Jul. 2008).
Lowe et al., "Synthesis and profiling of a diverse collection of azetidine-based scaffolds for the development of CNS-focused lead-like libraries," J Org Chem., 77:7187-211 (Sep. 7, 2012) (Author Manuscript).
Lu et al., "Tracking single hematopoietic stem cells in vivo using high-throughput sequencing in conjunction with viral genetic barcoding," Nature Biotechnol., 29(10):928-934 (Oct. 2011).

(Continued)

*Primary Examiner* — Frank W Lu
(74) *Attorney, Agent, or Firm* — Fish & Richardson P.C.

(57) ABSTRACT

Methods to simultaneously test and screen multiplexed, mixed cell populations, e.g., populations comprising genetically heterogeneous cancer cells, in common conditions.

10 Claims, 19 Drawing Sheets

(56) References Cited

OTHER PUBLICATIONS

Marcaurelle et al., "An aldol-based build/couple/pair strategy for the synthesis of medium- and large-sized rings: discovery of macrocyclic histone deacetylase inhibitors," J Am Chem Soc., 132:16962-76 (Dec. 1, 2010) (Author Manuscript).

McDermott et al., "Identification of genotype-correlated sensitivity to selective kinase inhibitors by using high-throughput tumor cell line profiling," Proc Natl Acad Sci USA 104(50):19936-19941 (Dec. 11, 2007).

Muellner et al., "A chemical-genetic screen reveals a mechanism of resistance to PI3K inhibitors in cancer," Nature Chem Biol., 7:787-793 (Nov. 2011).

Peck et al., "A method for high-throughput gene expression signature analysis," Genome Biol., 7:R61; 6 pages (Jul. 2006).

Schreiber et al., "Towards patient-based cancer therapeutics," Nat Biotechnol., 28:904-6 (Sep. 2010) (Author Manuscript).

Sos et al., "Predicting drug susceptibility of non-small cell lung cancers based on genetic lesions," J Clin Invest, 119(6):1727-1740 (Jun. 2009).

Yamamoto et al., "Color coding cancer cells with fluorescent proteins to visualize in vivo cellular interaction in metastatic colonies," Anticancer Res., 24:4067-72 (Nov.-Dec. 2004).

Yu et al. "Decoding cancer vulnerabilities simultaneously in mixtures of barcoded tumor cell lines with PRISM," Abstract, The Second East Coast Academic Screening Symposium, 1 page, Sep. 28, 2011.

Yu et al. "Decoding cancer vulnerabilities simultaneously in mixtures of barcoded tumor cell lines with PRISM," Abstract and Presentation, Nat'l Cancer Institute Integrative Cell Biology Program Junior Investigators' Meeting, Nov. 2, 2011, 50 pages.

Yu et al., "High-throughput identification of specific cancer vulnerabilities in mixtures of DNA-barcoded solid tumor cell lines using PRISM," Abstract, 5th Annual Multi-institutional Prostate Cancer Program Retreat, 2 pages, Mar. 19-21, 2012.

Yu et al., "Novel Integrated Approaches for Identifying Small Molecules that Specifically Target Oncogenic KRAS function," Poster, 2010, 1 page.

David et al., "Profiling the relative drug sensitivities of varied cell lines simultaneously," Poster, 2009, Retrieved from the Internet: https://www.broadinstitute.org/files/shared/education/summerinterns/presentations/david-poster-2009.pdf, 1 page.

* cited by examiner

MULTIPLEX METHODS TO ASSAY MIXED CELL POPULATIONS SIMULTANEOUSLY

CROSS-REFERENCE TO RELATED APPLICATIONS

This application is a U.S. National Phase Application under 35 U.S.C. § 371 of International Patent Application No. PCT/US2013/031312, filed on Mar. 14, 2013, which claims the benefit of U.S. Provisional Patent Application No. 61/612,013, filed on Mar. 16, 2012. The entire contents of the foregoing are hereby incorporated by reference.

FEDERALLY SPONSORED RESEARCH OR DEVELOPMENT

This invention was made with government support under Grant Nos. P01CA089021, P50CA020381, U54CA112962, RL1-CA133834, RL1-GM084437, and UL1-DE019585 awarded by the National Institutes of Health. The government has certain rights in the invention.

TECHNICAL FIELD

This invention relates to methods that use multiplexed, mixed cell populations, e.g., populations comprising genetically heterogeneous cancer cells, to assess response in vivo and in vitro allowing use of screening methods to efficiently and cost-effectively determine relative reaction of cell populations in the mixture to common conditions within each sample. The methods are called herein "PRISM."

BACKGROUND

As similar cancers from different individuals may respond differently to the same agent because of unique genetic vulnerabilities in the cancer, there is a great unmet need to elucidate the effectiveness of new anticancer agents using multiple representative cancer models. While recent technologies have improved the processivity of cytotoxicity analyses of compounds (see, e.g., Sharma et al., Nature Reviews Cancer, 10:241, 2010), these tests remain expensive, laborious, or both.

SUMMARY

At least in part, the present invention is based on the development of screening methods for use with mixed cell populations. The methods described herein were designed to harness the multiplexing capability of nucleic acid tags, e.g., DNA barcodes, for large-scale in vitro and in vivo screens. The method uses stably integrated DNA barcode sequences to allow simultaneous assay of multiple cell lines to be performed in the same well of a tissue culture plate or in the same tumor of a mouse using the barcode solely as a unique and quantifiable marker for cell number. Detection of the number of cells in each population allows sensitivities of diverse cell lines to be assessed from the complex mixture of coexisting tumor cell lines treated together in vivo or in vitro significantly reduces the time and cost required to evaluate a large number of variables, e.g., evaluation of new and existing potential therapeutics and combinations thereof across multiple tumor cell lines.

Thus, in a first aspect, the invention provides methods for simultaneously determining the effect of a test condition on viability or proliferation of each of a plurality of genetically heterogeneous cell types. The methods include:

providing a unitary sample comprising a plurality of, e.g., five, ten, twenty, twenty-five, or more, genetically heterogeneous cell types (each individual cell type is genetically homogeneous within itself, but differs from the others in the plurality), wherein each cell type further comprises:
  (i) an exogenous nucleic acid tag stably integrated into the genome of the cells, e.g., a tag comprising a core sequence that is unique to each cell type, and flanking amplification primer binding sequences that are the same in all of the cells of the plurality, and
  (ii) optionally, a marker, e.g., a selectable or detectable marker;
and a known number of cells of each cell type is present in the sample;
exposing the sample to a test condition for a selected time; and
detecting a level of the exogenous nucleic acid tag in each cell type, wherein the level of the exogenous nucleic acid tag is proportional to the number of living cells in the sample after exposure to the test condition; and comparing the number of living cells in the sample after exposure to the test condition to a reference number of cells. The number of living cells in the sample after exposure to the test condition as compared to the reference number of cells indicates the effect of the test condition on viability or proliferation of each cell type.

In a further aspect, the invention provides methods for simultaneously determining the effect of a test condition on viability or proliferation of each of a plurality of genetically heterogeneous cell types. The methods include providing a unitary sample comprising a plurality of, e.g., five, ten, twenty, twenty-five, or more, genetically heterogeneous cell types, wherein each cell type further comprises:
  (i) an exogenous nucleic acid tag stably integrated into the genome of the cells, e.g., comprising a core sequence that is unique to each cell type, and flanking amplification primer binding sequences that are the same in all of the cells of the plurality, and
  (ii) optionally, a selectable or detectable marker;
and a known number of cells of each cell type is present in the sample; implanting the sample into a living animal; exposing the sample to a test condition for a selected time; harvesting the sample from the animal; and detecting a level of the exogenous nucleic acid tag in each cell type of the sample, wherein the level of the exogenous nucleic acid tag correlates to the number of living cells in the sample after exposure to the test condition; and comparing the number of living cells in the sample after exposure to the test condition to a reference number of cells. The number of living cells in the sample after exposure to the test condition as compared to the reference number of cells indicates the effect of the test condition on viability or proliferation of each cell type.

In yet a further aspect, the invention provides methods for simultaneously determining the relative effect of a test condition on viability or proliferation of each of a plurality of genetically heterogeneous cell types. The methods include providing a unitary sample comprising a plurality of, e.g., five, ten, twenty, twenty-five, or more, genetically heterogeneous cell types, wherein each cell type further comprises:
  (i) an exogenous nucleic acid tag stably integrated into the genome of the cells, e.g., comprising a core sequence that is unique to each cell type, and flanking amplification primer binding sequences that are the same in all of the cells of the plurality, and
  (ii) optionally, a selectable or detectable marker;

and a known number of cells of each cell type is present in the sample; exposing the sample to a test condition for a selected time; and detecting a level of the exogenous nucleic acid tag in each cell type of the sample, wherein the level of the exogenous nucleic acid tag correlates to the number of living cells in the sample after exposure to the test condition; assigning a value to the number of cells, e.g., based on calculation of AUC, hierarchical clustering, k-means clustering, or regression analysis; and ranking the cell types based on the value.

In some embodiments of the methods described herein, the reference number of cells represents a number of cells present in the sample at the end of the selected time in the absence of the test condition.

In some embodiments of the methods described herein, exposing the sample to a test condition comprises contacting the sample with a test compound or altering an environmental condition affecting the sample.

In some embodiments of the methods described herein, detecting a level of the exogenous nucleic acid tags comprises: amplifying the tags using pairs of primer that specifically amplify each of the nucleic tags present in the sample; and quantifying the amplified nucleic acids.

In some embodiments of the methods described herein, at least one of each pair of primers comprises a functional group, e.g., biotin, for attachment to a solid surface having a reactive group that links to the functional group, e.g., streptavidin.

In some embodiments of the methods described herein, the solid surface is a detectably labeled bead.

In some embodiments of the methods described herein, each cell in the sample attaches to a bead that is uniquely labeled for the cell type of that cell.

In some embodiments of the methods described herein, quantifying the amplified nucleic acids comprises contacting the amplified nucleic acids with a plurality of detectable oligonucleotides comprising sequences complementary to each of the cell types in the plurality of genetically heterogeneous cell types, wherein the detectable oligonucleotides comprise a label that uniquely corresponds to the cell type to which it is complementary; and quantifying an amount of detectable oligonucleotides bound to amplified nucleic acids.

In some embodiments of the methods described herein, each detectable oligonucleotides comprises a fluorescent microsphere, and the method comprises detecting emission from the fluorescent microspheres in the sample.

In some embodiments, the methods described herein further include simultaneously running a control sample in parallel, wherein the control sample does not include amplified nucleic acids, detecting fluorescent emission from the control sample, and subtracting the fluorescent emissions in the control sample from the emissions detected in the test sample.

In some embodiments, the methods described herein further include contacting the amplified nucleic acids with a plurality of detectable oligonucleotides at 45° C.

In some embodiments, the methods described herein further include contacting the amplified nucleic acids with a plurality of detectable oligonucleotides for at least 6, 8, 10, 12, or more hours.

In some embodiments, the methods described herein further include heating the sample to 95° C., e.g., for 15 minutes, prior to amplification.

In some embodiments of the methods described herein, the plurality of genetically heterogeneous cell types comprises cells from at least two different tissue types.

In some embodiments of the methods described herein, the plurality of genetically heterogeneous cell types comprises cells from at least two different tumor types.

The invention provides several advantages. The modular, scalable, and adaptable strengths of the methods described herein facilitate cancer drug discovery across multiple genetic backgrounds, allowing identification of new classes of therapeutics as well as better biologic understanding which will guide more precise personalized treatment strategies for cancer patients. The PRISM method described here offers multiple functionalities beyond current approaches to profiling the sensitivity of large panels of cancer cell lines to candidate compounds. For example, PRISM makes it feasible to rapidly test chemical analogs (made during medicinal chemistry optimization processes) across an entire cell line panel, thus assuring that the expected pattern of activity is retained in the optimized compound. Without PRISM, this is extremely difficult to do rapidly (requiring the growth and testing of hundreds of individual cell lines, compared to expansion of a single vial of pooled, barcoded cells), and thus is generally not done at all. In addition, it should be possible to screen entire compound libraries against a PRISM panel, thereby identifying candidate compounds based solely on their ability to differentially kill particular subsets of cancer cells. Furthermore, the PRISM method can be extended to other types of cellular perturbation, including genetic perturbation (e.g., with shRNAs). The latter may greatly enable the identification of genotype-specific dependencies.

Unless otherwise defined, all technical and scientific terms used herein have the same meaning as commonly understood by one of ordinary skill in the art to which this invention belongs. Methods and materials are described herein for use in the present invention; other, suitable methods and materials known in the art can also be used. The materials, methods, and examples are illustrative only and not intended to be limiting. All publications, patent applications, patents, sequences, database entries, and other references mentioned herein are incorporated by reference in their entirety. In case of conflict, the present specification, including definitions, will control.

Other features and advantages of the invention will be apparent from the following detailed description and figures, and from the claims.

DESCRIPTION OF DRAWINGS

The patent or application file contains at least one drawing executed in color. Copies of this patent or patent application publication with color drawing(s) will be provided by the Office upon request and payment of the necessary fee.

3b, Oncogene mutations in the EGFR gene were determined previously for 100 cell lines (3) and used to stratify responses to specific compounds shown. Boxplots show medians, 25th, and 75th percentiles, with bars showing standard error of the mean. PRISM, Nuclei, and ATP demonstrated trends toward reductions in cell viability with the EGFR inhibitor erlotinib in EGFR mutant lines compared to EGFR wild-type lines (not statistically significant).

Figure 3A:
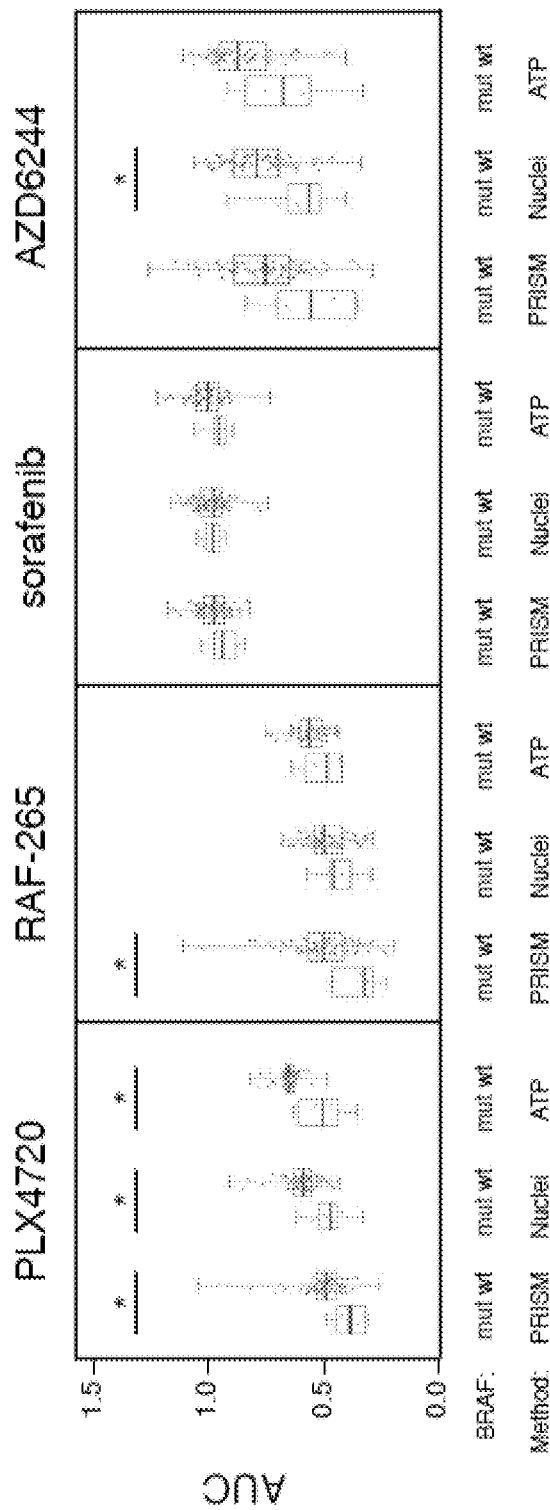
FIGS. 3a-b. Comparison of genotype-predicted responses of cell lines to targeted anticancer drugs, as determined by three cell viability measures. 3a, Oncogene mutations in the BRAF genes were determined previously for 100 cell lines (Barretina et al., 2012) and used to stratify responses to specific compounds shown. Boxplots show medians, 25th, and 75th percentiles, with bars showing standard error of the mean. PRISM, Nuclei, and ATP demonstrated significant (two-tailed t-test, asterisk denotes p<0.05) reductions in cell viability with the BRAF inhibitor PLX4720 in BRAF V600E mutant lines compared to BRAF wild-type lines; a similar reduction was seen only with PRISM with the RAF inhibitor RAF-265. The RAF inhibitor sorafenib did not demonstrate significant reductions in BRAF-mutant vs. -wild-type lines. The MEK inhibitor AZD6244 demonstrated significant reduction in BRAF V600E mutant lines compared to BRAF wild-type lines with CTG but only a trend towards this reduction in both PRISM and Nuclei.
Figure 3B:
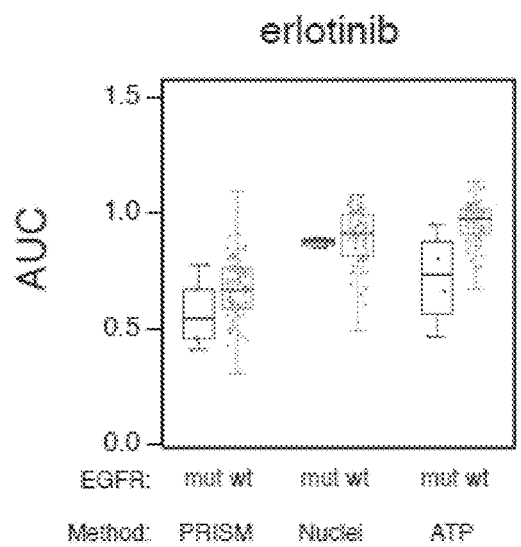
Figure 3C:
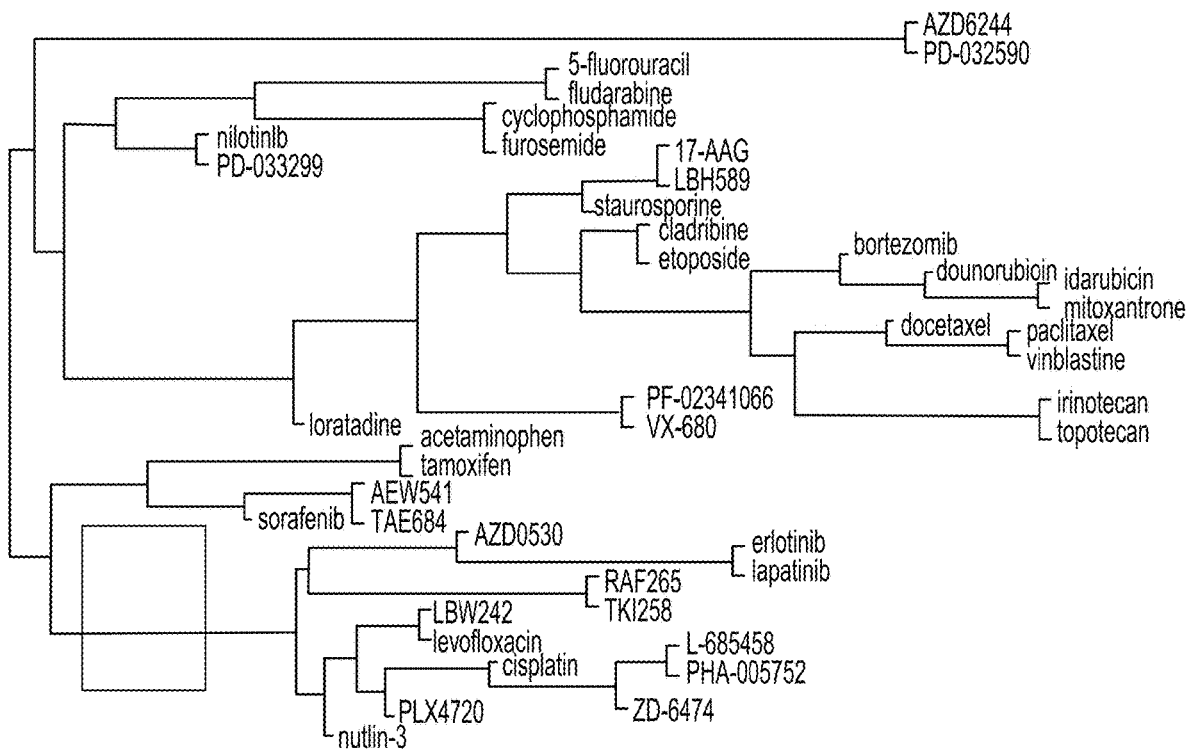

FIG. 3c, Hierarchical clustering of 43 anticancer and control compounds based on AUC measurements of 100 cell lines performed with PRISM (see text for details).

Figure 4A:
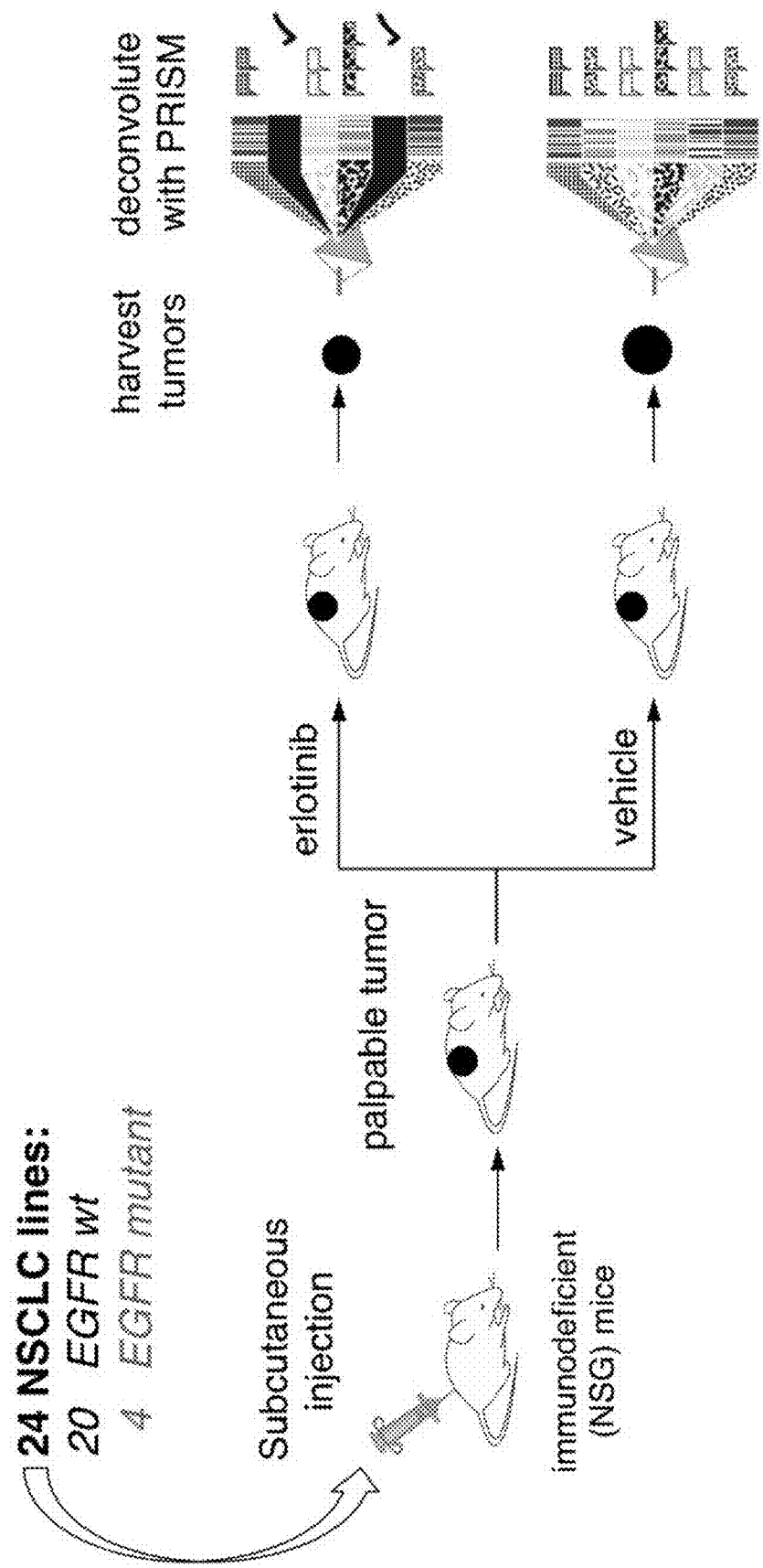

FIG. 4a, Schema for in vivo PRISM experiment. Twenty-four barcoded human lung adenocarcinoma cell lines were mixed together and $10^6$ cells per cell line (total, $2.4 \times 10^7$ cells) were injected subcutaneously into 20 immunodeficient NSG (NOD scid IL-2 receptor gamma chain) knockout mice. After tumors were palpable (~1 cm diameter), mice were treated with daily oral gavage with either erlotinib at 50 mg/kg or vehicle. Tumors were harvested approximately 2 weeks later, and PRISM analysis was performed.

Figure 4B:
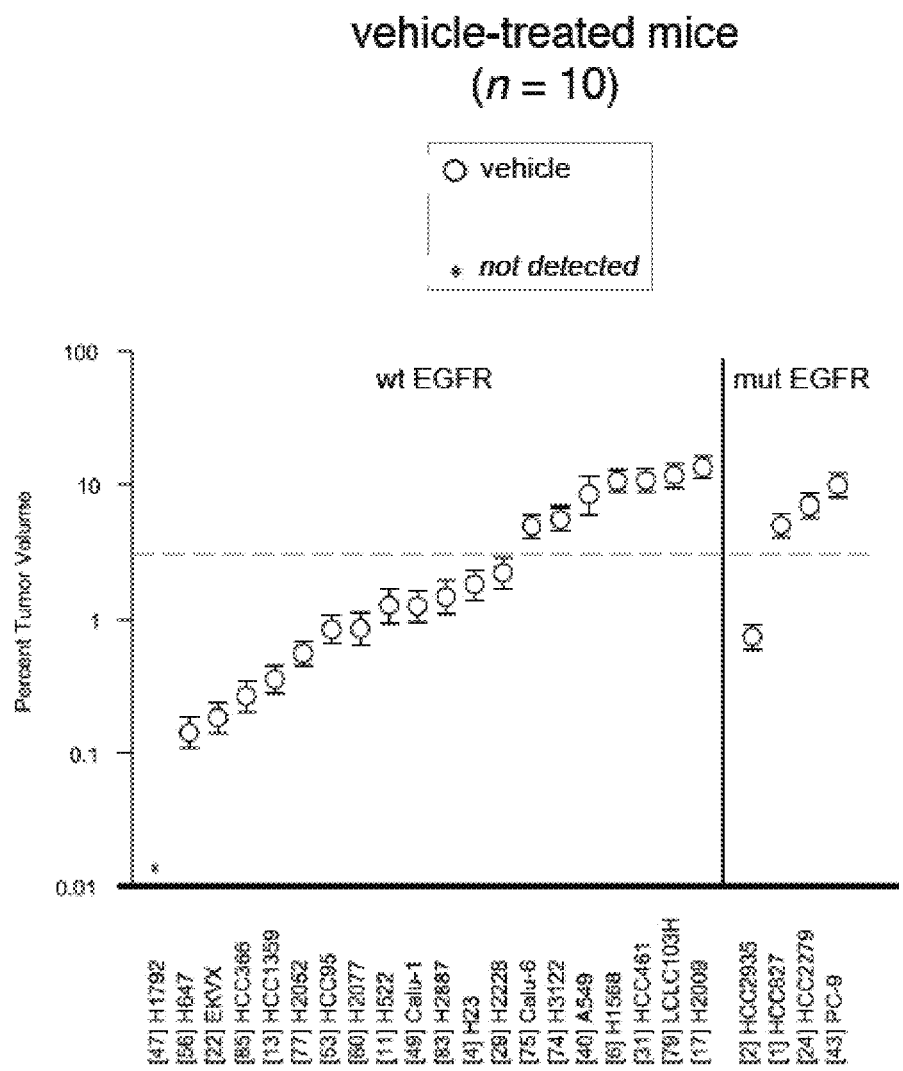

FIG. 4b, Relative tumor cell line growth in mixture. PRISM was used to quantitate barcode signals from tumors in vehicle-treated animals. Tumor barcode signals were scaled first to corresponding barcode signals of the injected cell mixture to determine the number of cell equivalents; the scaled signal for each barcode line was then used to determine the percentage contribution of each tumor cell line to the mixture. The same 23 of 24 lines were detected in all 10 vehicle-treated animals. Circles denote mean percentage tumor volume; error bars denote standard error of the mean. Dotted line denotes the percentage contribution at injection (with all lines in equal proportion) for comparison.

Figure 4C:
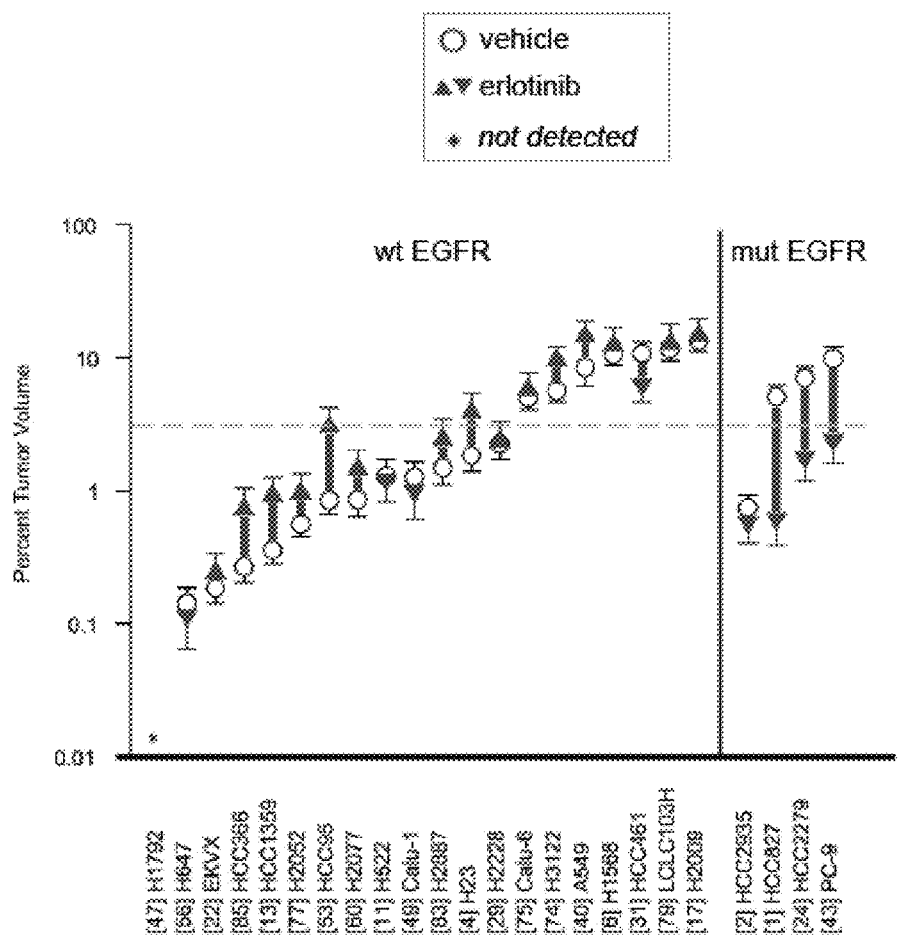

FIG. 4c, Relative tumor cell line growth in mixture. Tumors from erlotinib-treated animals were compared to those from vehicle-treated animals as in b.

Figure 5A:
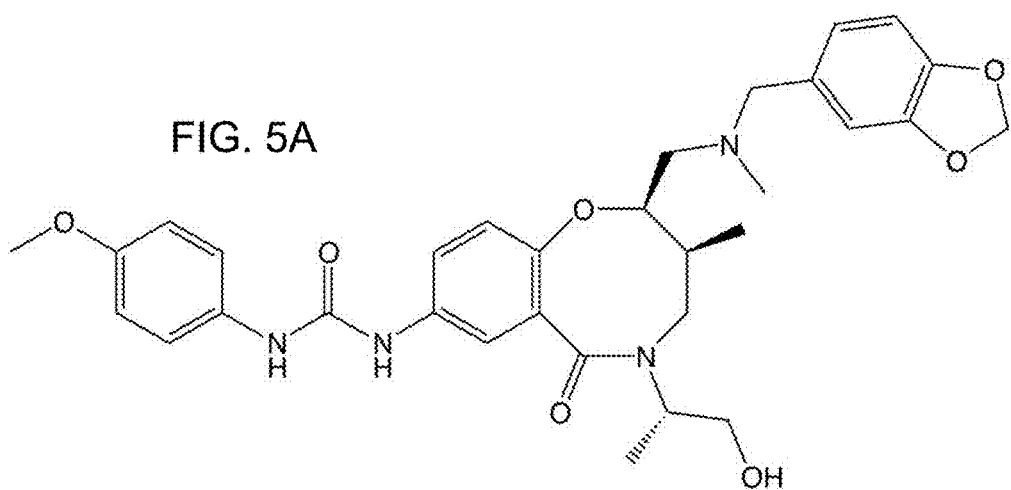

FIG. 5a, Structure of BRD-7880.

Figure 5B:
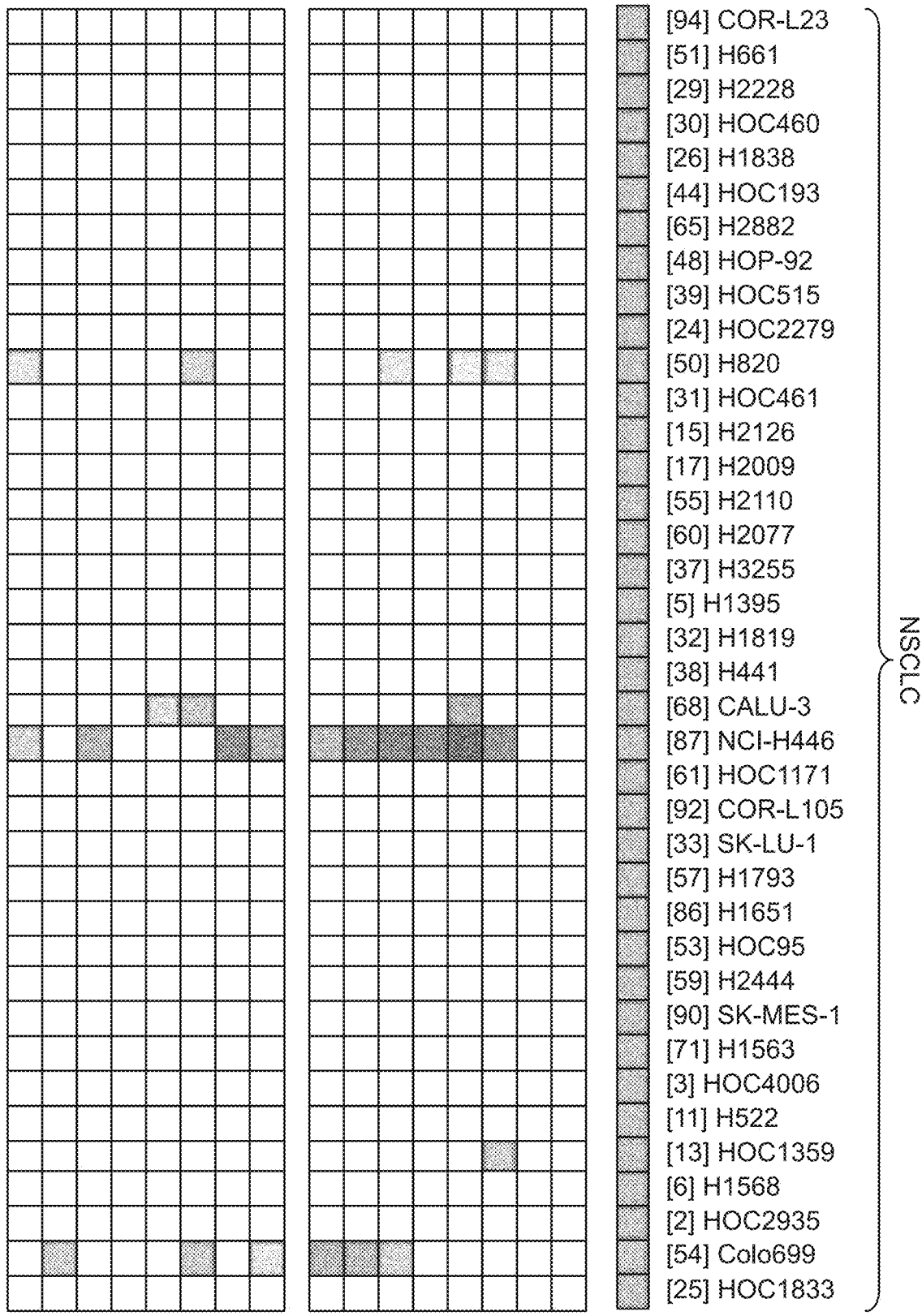
Figure 5B:
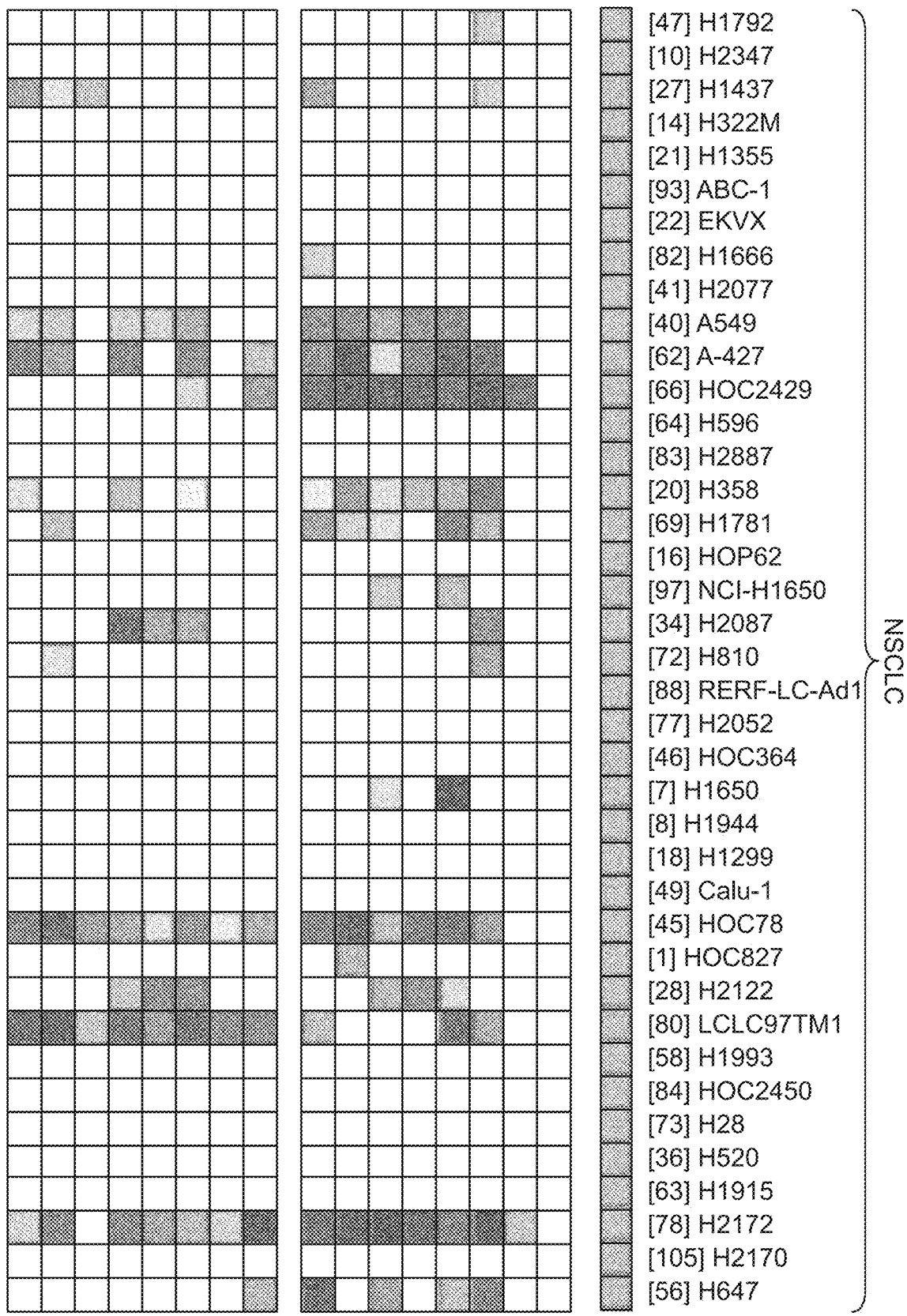
Figure 5B:
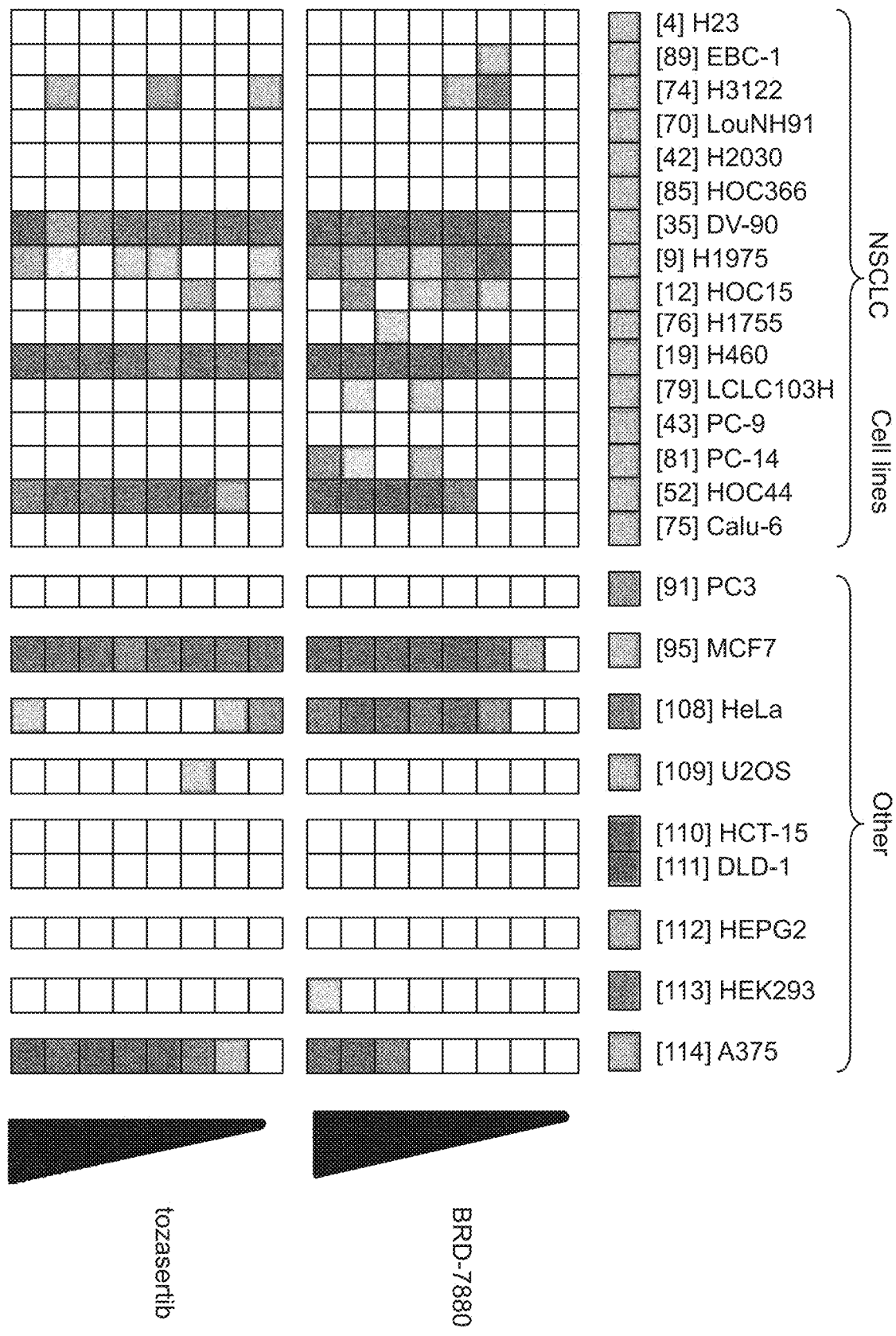

FIG. 5b, Comparison of PRISM profiles across 102 cell lines for BRD-7880 (0.25, 0.5, 1, 2, 4, 8, 16, 32 μM) or tozasertib (0.06, 0.13, 0.26, 0.52, 1, 2, 4, 8 μM).

Figure 5C:
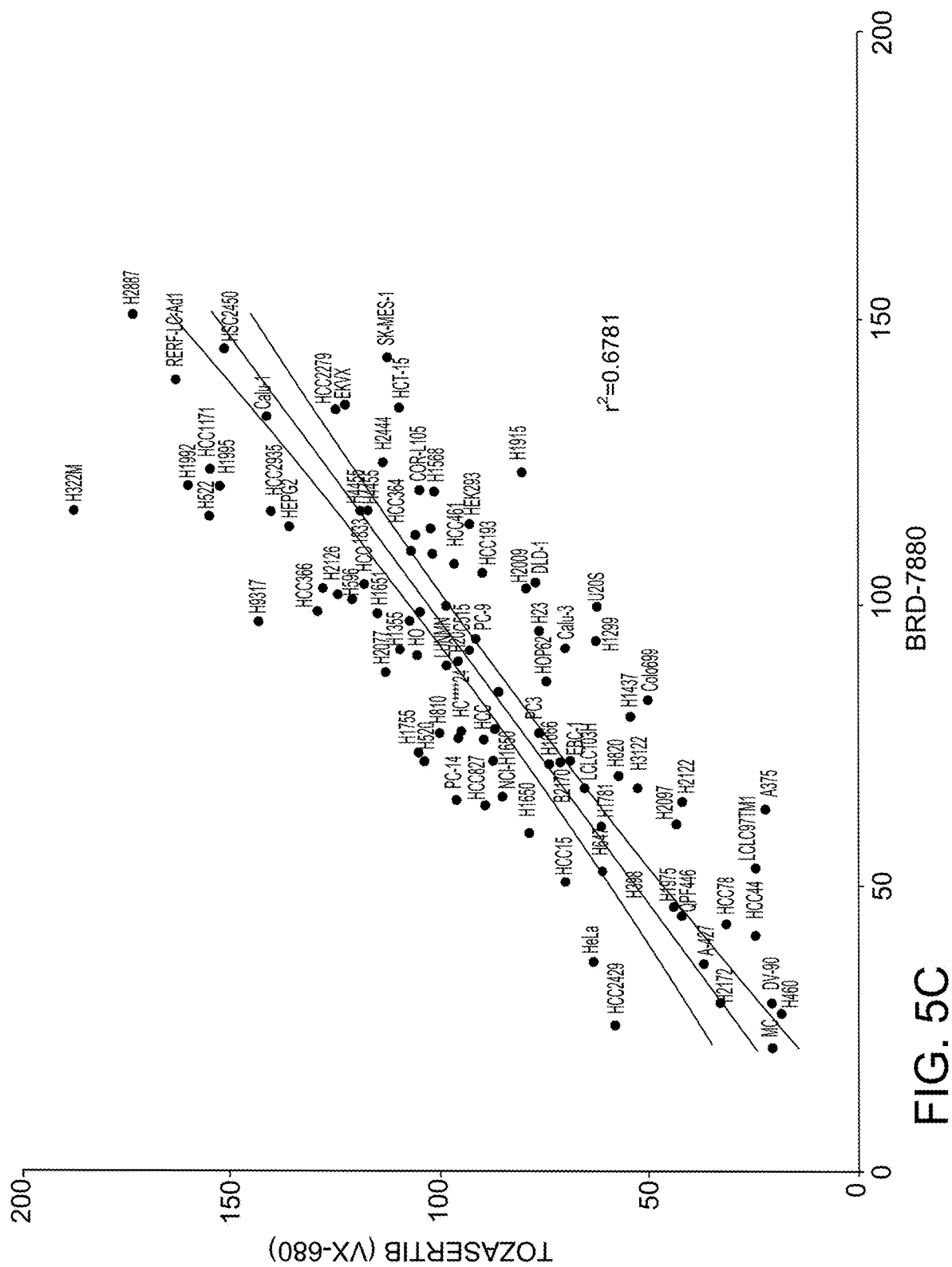

FIG. 5c, Correlation of PRISM AUC between BRD-7880 and tozasertib. Area under the curve (AUC) of viability vs. concentration curve was calculated for each cell line across 8 doses of compound. Spearman correlation $r^2=0.6781$.

Figure 5D:
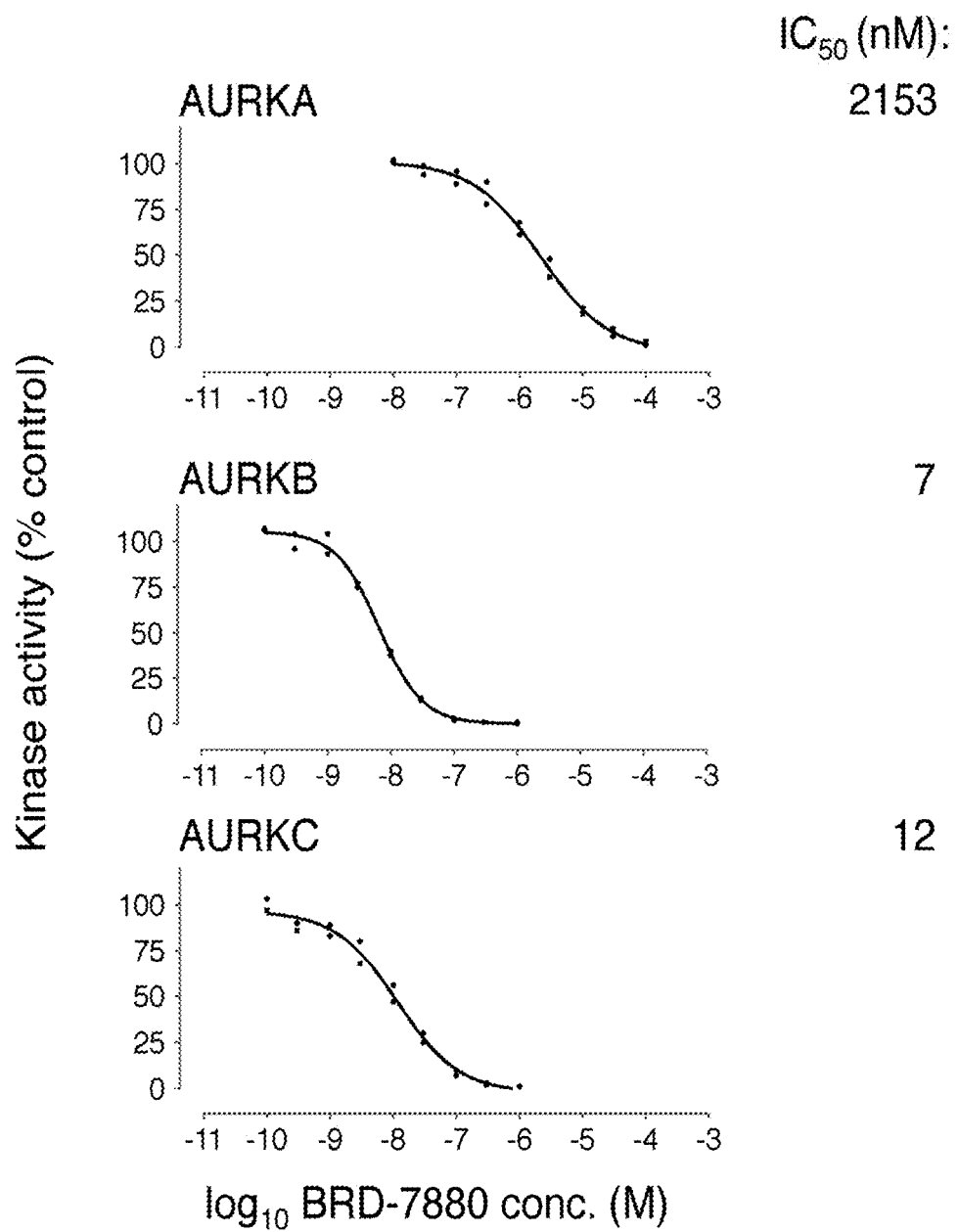

FIG. 5d, In vitro aurora kinase assays. Incorporation of radioactivity from 10 μM γ-$^{33}$P-ATP was measured in in vitro kinase assays across 8 doses in duplicate by the EMD Millipore KinaseProfiler service (Billerica, Mass.) under published standard conditions with 10 mM ATP. Full-length human aurora-A was assayed with 200 μM LRRASLG (Kemptide); full-length human aurora-B with 30 μM AKRRRLSSLRA (ribosomal protein S6 peptide); and full-length human aurora-C with 30 μM AKRRRLSSLRA. $IC_{50}$ values were modeled using least-squares and variable slope with Prism 6.0 software (GraphPad, San Diego, Calif.).

Figure 5E:
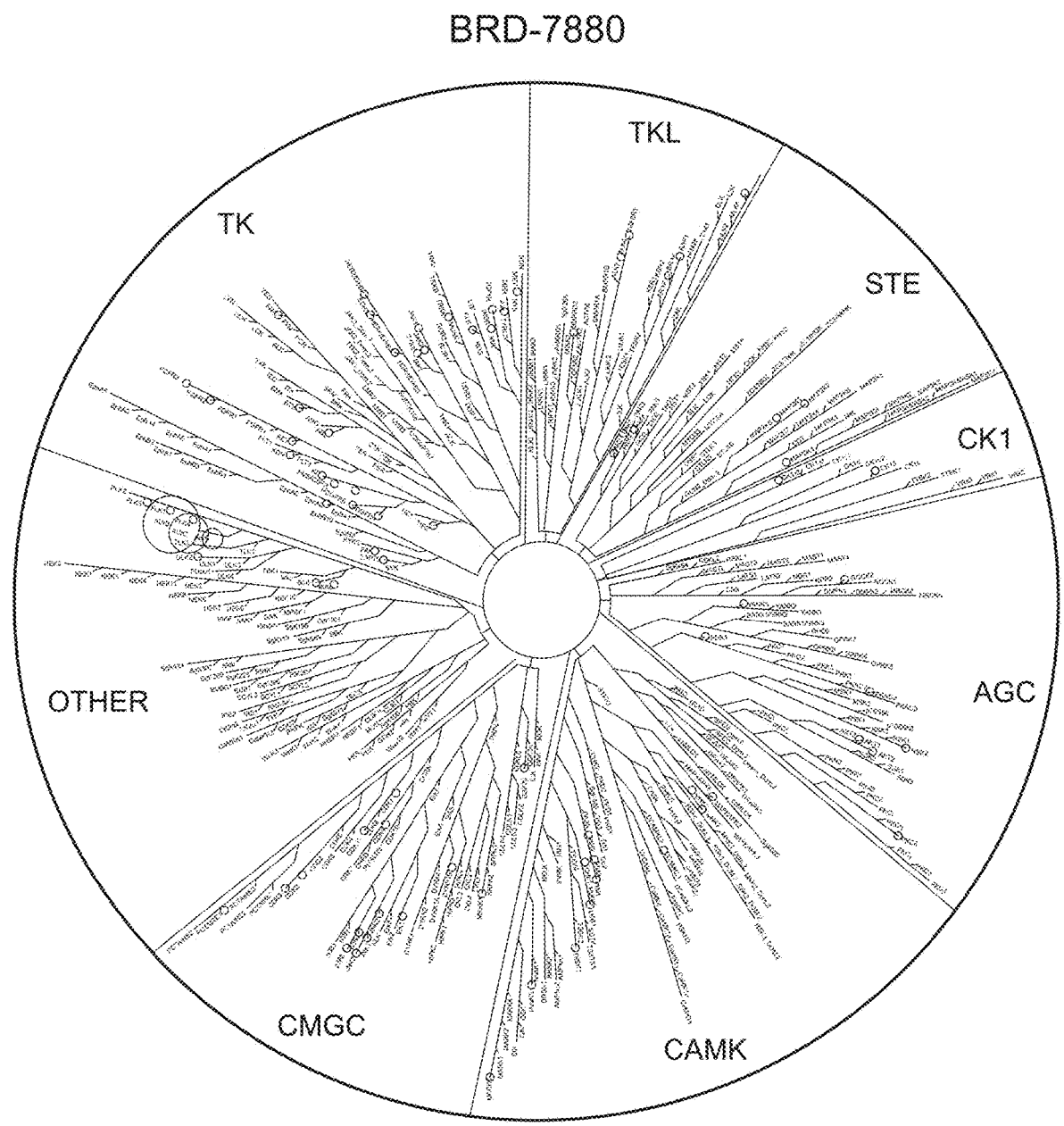
Figure 5F:
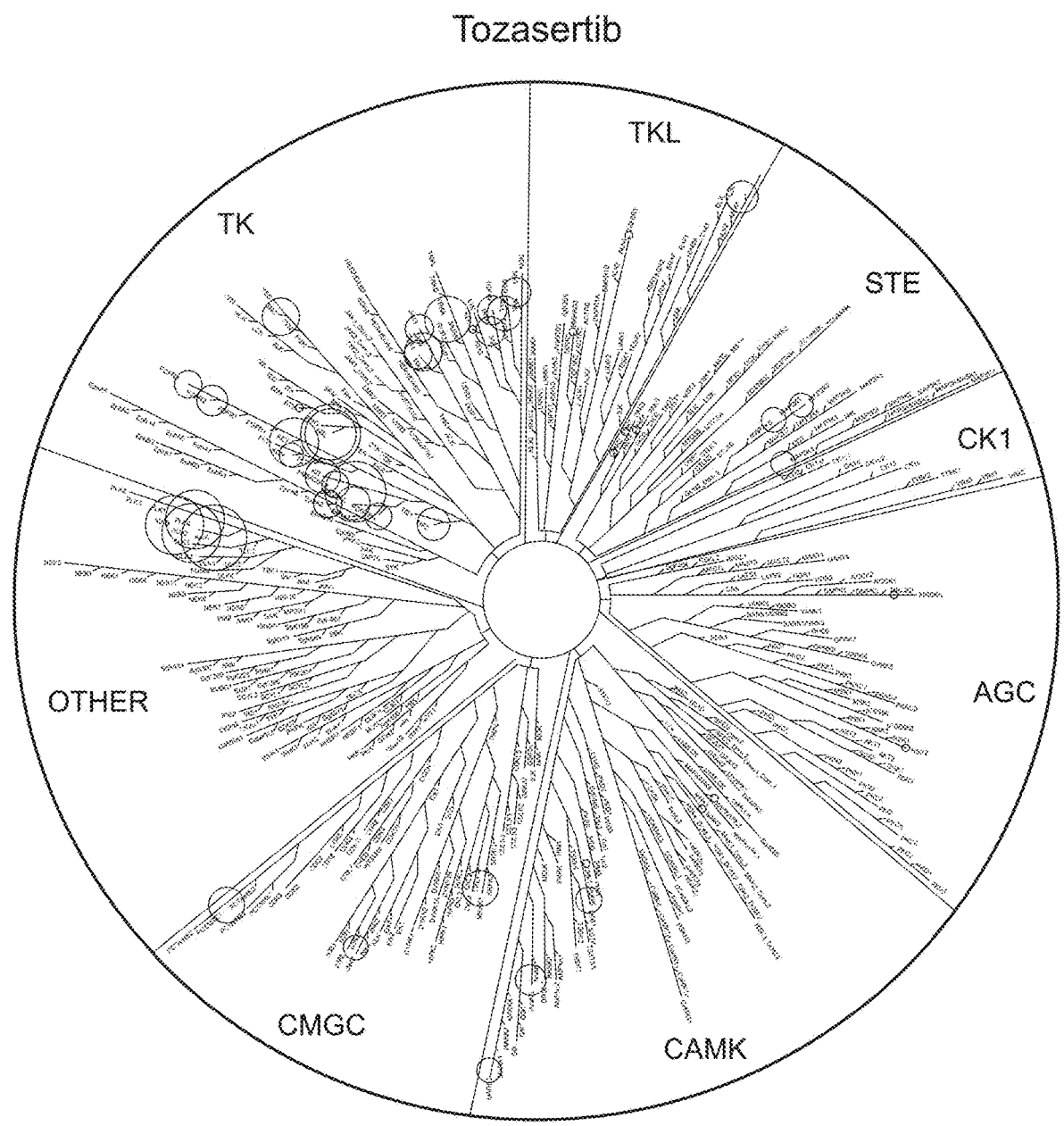

FIGS. 5*e-f*, KinomeScan profile for BRD-7880 and tozasertib across 98 kinases. Schematic representation of relative affinity of BRD-7880 (5*e*) and tozasertib (5*f*) for specific kinases in the KinomeScan assay. Dark grey circles represent tested kinases for which BRD-7880 or tozasertib decreased binding of control inhibitor by more than 75%.

Figure 5G:
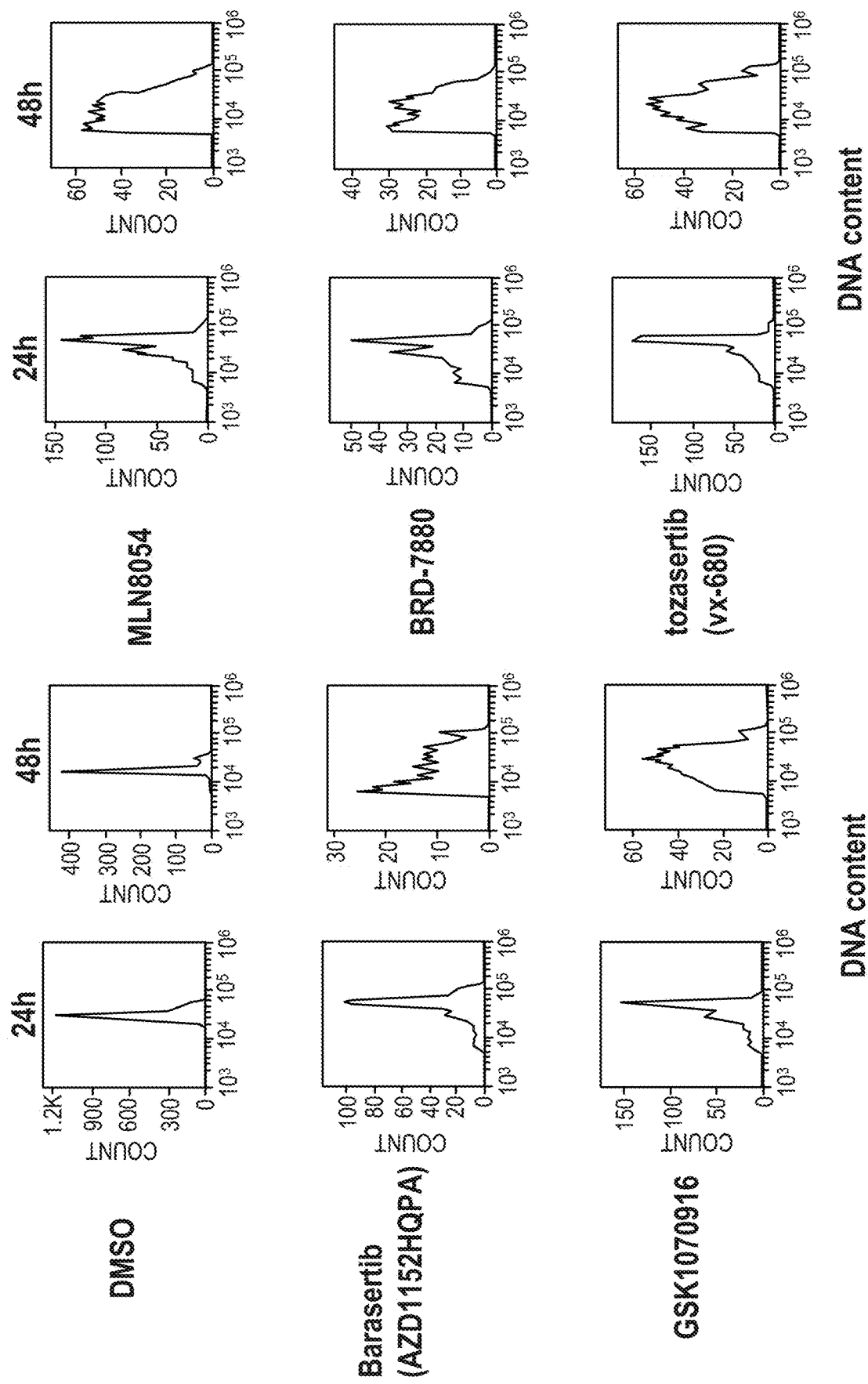

FIG. 5*g*, BRD-7880 and the other aurora kinase inhibitors increased DNA content of HCT-116 cells.

Figure 5H:
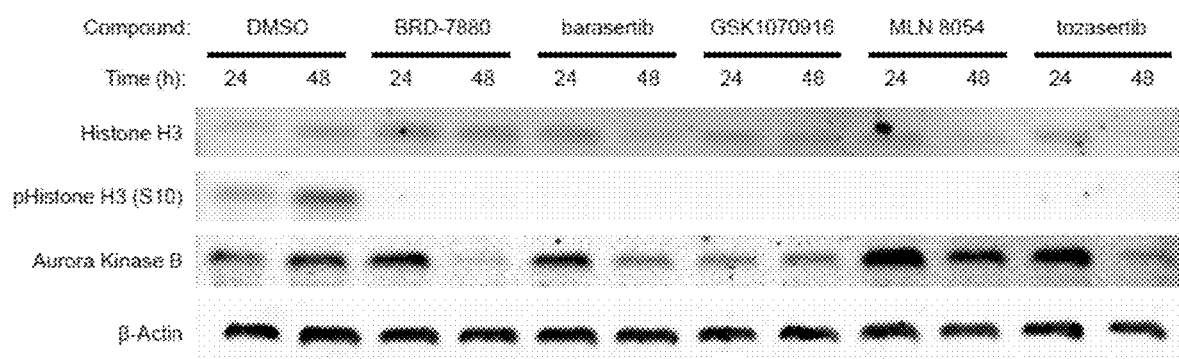

FIG. 5*h*, BRD-7880 and other aurora kinase inhibitors decrease phosphorylation of serine 10 on histone H3, a marker of aurora B kinase activity.

Figure 6:
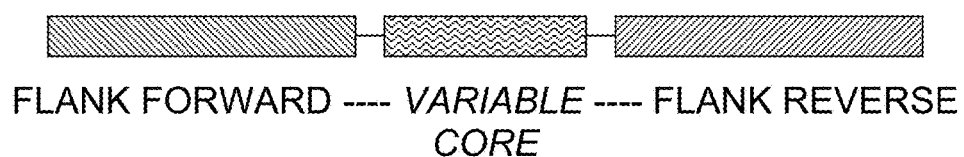

FIG. 6, schematic illustration of an embodiment in which the nucleic acid tags include flanking sequences that allow binding of a set of primers for amplifying the variable, unique core sequence.

Figure 7:
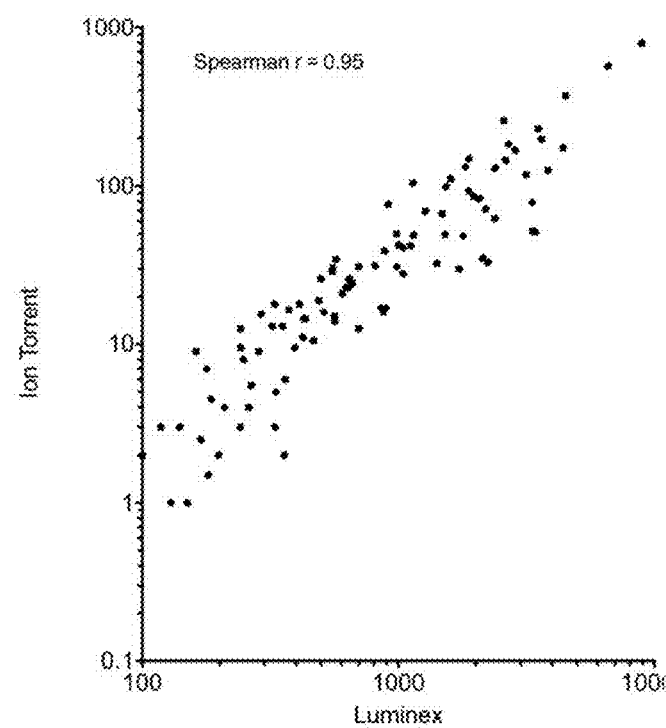

FIG. 7. Comparison of PRISM quantification of barcoded tumor cell lines with Luminex bead hybridization vs. sequencing. The two methods demonstrate similar relative numbers of barcodes (Spearman r=0.95).

DETAILED DESCRIPTION

While barcoding methods have been used extensively to allow parallel, multiplexing experimentation of different types of genetic alterations (e.g., Craig et al., Nat. Methods 5, 887-893 (2008); Gerrits et al. Blood 115, 2610-2618 (2010); Berns et al., Nature 428, 431-437 (2004), the methods described herein, referred to as PRISM, were designed to harness the multiplexing capability of nucleic acid tags, e.g., DNA barcodes, for large-scale in vitro and in vivo screens as quantifiable surrogates for specific cell types in a heterogeneous mixture. Lentiviral barcoding vectors allow stable (e.g., via blasticidin selection) integration of nucleic acid tags, e.g., DNA barcode sequences of about 24-basepairs that are preferably engineered to minimally crosshybridize. To permit greater detection sensitivity while minimizing amplification bias, all barcodes are amplified with the same common primers to yield uniform amplicon lengths.

As described herein, cell line responses in mixture determined by PRISM correlate well with two independently validated measures of response (CTG or OPTICAL) performed with the same cell lines examined individually. There was slightly stronger correlation between PRISM and OPTICAL (both of which enumerate nuclei) than between PRISM and CTG (the latter of which measures ATP as a surrogate for the number of viable cells). Except for two compounds (paclitaxel and topotecan) there was generally no pattern to any discrepancies between AUC measured with PRISM versus AUC measured with the other methods.

The methods described herein are readily adaptable to facilitate multiple avenues of inquiry. Starting with an active small molecule, one could rapidly determine which cell line(s) could serve as models for further biological or biochemical studies. An active agent used in a particular type of cancer could be tested with the present on a mixture of cell lines from multiple cancers to rapidly identify other cancers where this agent might also be effective. A diverse collection of tagged, e.g., barcoded cell lines could be used to profile thousands of small molecules to identify functional similarities between small molecules and molecular structural determinants of activity. Orthogonal analyses of genetic changes (copy number alterations, genetic mutations, changes in gene expression) may be analyzed together with functional data derived from hundreds of cell lines with sufficient power to find statistically significant genotype-phenotype correlations. Genetic knockdown experiments using shRNA or siRNA methods could be performed simultaneously across many cell contexts and cells could serve as internal controls for the presence of adequate viral titers.

The significant reductions in scale afforded by the present methods enable rigorous studies of therapeutic combinations using pairs of small molecules at multiple doses, or the combination of a small molecule and a specific genetic alteration (e.g., knockdown or overexpression), simultaneously in a large number of different cell types.

Genetically Heterogeneous Cell Types

The methods described herein include simultaneously assaying, in a single unitary (undivided) sample, a plurality of genetically heterogeneous cell types. As used herein, a plurality of genetically heterogeneous cell types means a mixed population of at least two, e.g., 3, 4, 5, 6, 7, 8, 9, 10, 15, 20, 25, 30, 35, 40, 45, 50, 55, 60, 65, 70, 75, 80, 85, 90, 95, 100, or more, cell types that have different endogenous genetic backgrounds. As used herein, genetic heterogeneity can refer to genomic heterogeneity (e.g., cells from different subjects, or harboring different mutations), epigenetic heterogeneity (e.g., cells that express different genes, different levels of genes, or have different epigenetic modifications), and/or phenotypic heterogeneity (e.g., cells from different tissues, different tumors, different subjects). In preferred embodiments, other than the presence of a nucleic acid tag, and optionally one or both of a selectable marker and a detectable marker, the cells have no other modifications, e.g., are otherwise identical to the parent cell or parental cell line from which they are derived.

Simultaneous assay of a heterogeneous mixture of cells presents theoretical challenges to execution and interpretation. Different cells grow at different rates and have different culture media requirements, thus the methods can include selecting and mixing populations of cells that can tolerate common growth conditions. Cells grown in mixture might affect each other through direct cell-cell interactions or through paracrine signaling, or death of one cell type in response to an exogenous agent might affect the viability of another; such effects can be accounted for by the presence of controls, either separate control samples or controls within each sample.

In the methods described herein, these challenges are properly accounted for, and the mixture assays described herein can provide exponentially significant reductions in the labor and cost of performing functional cell-based experiments. The methods permit simultaneous assays across many different genetic models in any laboratory. Furthermore, because all cells are cultured together and exposed to the same agent, the cells are able to serve as internal controls for others.

The present methods can use pools of barcoded adherent or nonadherent cells. Other types of experiments could use barcode signals as quantifiable markers of specific cells, such as evaluation of ecological changes within a tumor following a specific treatment, or the tracking of cells from a primary tumor which become metastases.

The methods can be performed on a sample that is maintained in an in vitro environment, e.g., a plurality of cells in culture together, wherein the test conditions are applied in vitro. Alternatively or in addition, the methods can be performed on cells that are maintained for a time in vivo, e.g., cells injected into an experimental animal, wherein the test conditions are applied in vivo. In such embodiments, at some time after application of the test conditions, the methods include isolating the cells from the animal and assaying the numbers of cells.

The methods can be performed on any type of cells, e.g., mammalian, or non-mammalian, e.g., avian, reptilian, or insect cells. As one example, the plurality of cell types can include tumor cells from different tumor types, different tissues, different genetic backgrounds, different subjects, and/or different stages of cancer. In some embodiments, the plurality of cell types includes control cells, e.g., normal cells, to identify compounds that are less toxic or not toxic to normal cells.

The plurality of cell types can comprise prokaryotic cells, e.g., bacteria, fungi, or protozoa. Where the plurality of cell types includes bacteria, the methods can be used to identify new antibiotics; in some embodiments, the cell types can include control bacterial that are non-pathogenic (e.g., normal gut flora), and compounds that kill pathogenic bacteria but don't substantially affect the non-pathogenic bacteria are preferentially selected.

Nucleic Acid Tags

Individual cell types (e.g., cell lines) can be labeled with any identifying nucleic acid tag, e.g., DNA barcode, and any combination of cell lines may be mixed together for assays so long as they are capable of growth in the same conditions—allows optimization for different applications. A number of nucleic acid tags are known in the art; in preferred embodiments the nucleic acid tag comprises a core of a sufficient number of nucleotides to provide specificity, e.g., 20-26 nucleotides, e.g., 22-24 nucleotides, and is designed to be both unique to each cell type, readily amplifiable (e.g., lacking in substantial predicted secondary structures such as hairpins), and not readily cross-hybridizable, to give results that can be specifically interpreted with confidence. In some embodiments, e.g., as shown in FIG. 6, the nucleic acid tags further comprise flanking sequences that allow binding of a set of primers for amplifying the variable, unique core sequence; in some embodiments, the flanking sequences are all the same in all of the cells of the plurality of genetically heterogeneous cell types (though the core sequences vary from cell type to cell type as described herein).

The tags can be integrated into the genome of the cells using methods known in the art, e.g., viral delivery vectors, e.g., retroviral or lentiviral vectors, as known in the art and described herein to achieve stable integration. Other methods can also be used, e.g., homologous or targeted integration, or integration using a recombinase such as the Cre-Lox, Flp-FRT, and zinc-finger recombinases (ZFRs); piggyBac and Sleeping Beauty transposon systems; and others. See, e.g., Gersbach et al., Nucleic Acids Research, 2011, 1-11 (doi: 10.1093/nar/gkr421); Wilson et al., Mol. Ther. 2007; 15:139-145; VandenDriessche et al., Blood 2009; 114:1461-1468; Bushman et al., Nat. Rev. Microbiol. 2005; 3:848-858; Yant et al., Nucleic Acids Res. 2007; 35:e50; Sauer et al., Proc. Natl Acad. Sci. USA 1988; 85:5166-5170; Logie et al., Proc. Natl Acad. Sci. USA 1995; 92:5940-5944; Thyagarajan et al., Mol. Cell. Biol. 2001; 21:3926-3934; Wu et al., Proc. Natl Acad. Sci. USA 2006; 103:15008-15013; and others. Cells that have the tag integrated into a non-deleterious part of the genome are preferred.

In some embodiments, the cells also include a selectable marker that allows identification and selection of cells that carry the nucleic acid tags. Positive or negative selection markers can be used. In some embodiments, an antibiotic resistance gene, e.g., that confers resistance to blasticidin S (blasticidin$^r$ gene, a blasticidin deaminase), neomycin (neo$^r$, neomycin phosphotransferase), or hygromycin B (hyg$^r$, hygromycin B phosphotransferase (HPH)). A number of others are known in the art. Detectable markers can also be used, e.g., fluorescent proteins, e.g., GFP and variants thereof including YFP, CFP, and RFP. In some embodiments, these markers are delivered to the cell using the same nucleic acid that includes the tag.

Detection and Quantification of Nucleic Acid Tags

Tag (e.g., barcode) detection can be readily performed using methods known in the art, e.g., using fluorescently labeled microbeads or high-throughput sequencing-based detection methods. For example, the Luminex XMAP technology can be used, in which fluorescent microbeads that are color-coded into distinct sets, each of which is tagged with a nucleic acid that hybridizes to a nucleic acid tag in one cell type of the plurality, allowing specific capture, detection, and quantification of that cell type. See, e.g., Lu, J. et al. MicroRNA expression profiles classify human cancers. Nature 435, 834-838 (2005). Nanostring technology can also be used, see, e.g., Geiss et al., Nat Biotechnol. 26:317-25 (2008). In some embodiments, high throughput methods, e.g., gene chips as are known in the art (see, e.g., Ch. 12, "Genomics," in Griffiths et al., Eds. *Modern genetic Analysis,* 1999, W. H. Freeman and Company; Ekins and Chu, Trends in Biotechnology, 1999, 17:217-218; MacBeath and Schreiber, Science 2000, 289(5485):1760-1763; Hardiman, *Microarrays Methods and Applications: Nuts & Bolts,* DNA Press, 2003), can be used. In some embodiments, e.g., where hybridization to fluorescent beads is used, the methods include contacting the nucleic acid tags, e.g., amplified nucleic acid tags, with a detection oligo comprising a complementary sequence that is detectable, e.g., a fluorescent microparticle, e.g., the Luminex XMAP technology. In some embodiments, instead of a bead, the detection oligo is labeled in another way, e.g., using a quantum dot that is uniquely tuned for each tag/cell type, such that the different cell types can be distinguished. In some embodiments, the oligo is linked to a solid surface such as a chip rather than a bead; this allows for additional methods of detection including surface plasmon resonance. The bead or solid surface can be attached to the detection oligos using any method known in the art, e.g., I-LINKER; amine-modified oligos that covalently link to an activated carboxylate group or succinimidyl ester on the bead; thiol-modified oligos that covalently link via an alkylating reagent, e.g., an iodoacetamide or maleimide to the bead; ACRYDITE-modified oligos that covalently link to the bead, e.g., through a thioether; digoxigenin NHS Ester linkage; cholesterol-TEG linker; and, in preferred embodiments, biotin-modified oligos that link to beads covered with streptavidin. In some embodiments, the primers used to amplify the nucleic acid tag are themselves modified for attachment to a bead or solid surface for detection.

Although bead-based barcode detection methods (e.g., LUMINEX) represent a robust and cost-effective approach, other detection methods, e.g., massive parallel sequencing, can be used.

In some embodiments, the methods of detection include a step of amplifying the nucleic acid tags. Nucleic acid amplification methods include, without limitation, polymerase chain reaction (PCR) (U.S. Pat. No. 5,219,727) and its variants such as in situ polymerase chain reaction (U.S. Pat. No. 5,538,871), quantitative polymerase chain reaction (U.S. Pat. No. 5,219,727), nested polymerase chain reaction (U.S. Pat. No. 5,556,773), self-sustained sequence replication and its variants (Guatelli et al., Proc Natl Acad Sci USA. 87:1874-8 (1990)), transcriptional amplification system and its variants (Kwoh et al., Proc Natl Acad Sci USA. 86:1173-7 (1989)), Qb Replicase and its variants (Miele et al., J Mol Biol. 171:281-95 (1983)), cold-PCR (Li et al., Nat Med. 14:579-84 (2008)), or any other nucleic acid amplification methods, followed by the detection of the amplified molecules using techniques well known to those of skill in the art.

The present methods can be performed using certain parameters, to optimize sensitivity, specificity, and precision to yield meaningful results, i.e., where the detected barcode signal accurately reflects the number of cells of each type. Both sensitivity and specificity should be sufficiently maximized to correctly identify the least prevalent cell moiety. With optimized protocols we have achieved greater than 60% sensitivity and 90% specificity in high throughput versus currently used non-multiplexed methods for enumerating viable cells. For example for optimization of sensitivity, where proteinase K is used in preparation of cell lysates, the samples can be boiled (e.g., by heating to 95° C., e.g., for 15 minutes) prior to amplification to allow maximum activity of polymerase. In some embodiments, the samples can be heated to 95° C. for 15 minutes, then cooled, e.g., to 10° C., and optionally centrifuged before amplification. This inactivates all proteinases (including any residual proteinase K from sample preparation) and increases sensitivity.

In some embodiments, the methods include running a control sample in parallel, wherein the control sample has no DNA template. The signal from this sample is then used as a "background" for subtraction, increasing sensitivity of the methods.

In some embodiments, the methods include a hybridization step wherein the amplified tags are contacted with detection oligos, e.g., bead-linked detection oligos, e.g., at 45° C. The methods can include allowing this hybridization step to proceed for at least 6, 8, 10, 12, or more hours, thereby increasing sensitivity.

In some embodiments, the methods include running a control sample without genomic DNA, where this signal is subtracted from sample signal, to improve specificity of the methods.

Test Conditions

Included herein are methods for screening various test conditions, to identify agents that affect numbers of cells. Test conditions that reduce numbers of cells, e.g., cancer or tumor cells, can be considered candidates for the treatment of cancer; if the conditions decrease the numbers of cell types from a specific type of cancer, then the condition is a candidate for the treatment of that specific type of cancer. In some embodiments, the test conditions comprise contacting the sample with one or more test compounds, e.g., polypeptides, polynucleotides, inorganic or organic large or small molecule test compounds.

As used herein, "small molecules" refers to small organic or inorganic molecules of molecular weight below about 3,000 Daltons. In general, small molecules useful for the invention have a molecular weight of less than 3,000 Daltons (Da). The small molecules can be, e.g., from at least about 100 Da to about 3,000 Da (e.g., between about 100 to about 3,000 Da, about 100 to about 2500 Da, about 100 to about 2,000 Da, about 100 to about 1,750 Da, about 100 to about 1,500 Da, about 100 to about 1,250 Da, about 100 to about 1,000 Da, about 100 to about 750 Da, about 100 to about 500 Da, about 200 to about 1500, about 500 to about 1000, about 300 to about 1000 Da, or about 100 to about 250 Da).

The test compounds can be, e.g., natural products or members of a combinatorial chemistry library. A set of diverse molecules can be used to cover a variety of functions such as charge, aromaticity, hydrogen bonding, flexibility, size, length of side chain, hydrophobicity, and rigidity. Combinatorial techniques suitable for synthesizing small molecules are known in the art, e.g., as exemplified by Obrecht and Villalgordo, *Solid-Supported Combinatorial and Parallel Synthesis of Small-Molecular-Weight Compound Libraries*, Pergamon-Elsevier Science Limited (1998), and include those such as the "split and pool" or "parallel" synthesis techniques, solid-phase and solution-phase techniques, and encoding techniques (see, for example, Czarnik, Curr. Opin. Chem. Bio. 1:60-6 (1997)). In addition, a number of small molecule libraries are commercially available. A number of suitable small molecule test compounds are listed in U.S. Pat. No. 6,503,713, incorporated herein by reference in its entirety.

The methods of the present invention can include screening a variety of types of test compounds, e.g., a library including a variety of compounds. A given library can comprise a set of structurally related or unrelated test compounds. In some embodiments, the test compounds are peptide or peptidomimetic molecules. In some embodiments, the test compounds are nucleic acids. In some embodiments, the test compounds are a combination (plurality) of compounds tested together.

Other test conditions can also be evaluated using the methods described herein, e.g., changes in environmental conditions including temperature, $O_2$ concentrations, $NO/N_2$ concentrations, or glucose concentrations.

As noted above, the methods can be performed on a sample that is maintained in an in vitro environment, e.g., a plurality of cells in culture together, wherein the test conditions are applied in vitro.

Alternatively or in addition, the methods can be performed on cells that are maintained for a time in vivo, e.g., cells injected into an experimental animal, wherein the test conditions are applied in vivo. In such embodiments, at some time after application of the test conditions, the methods include isolating the cells from the animal and assaying the numbers of cells. These in vivo applications can be used to reduce the number of animals required to test a given condition against a large number of cell types; thus, for example, the methods can be used to identify what cancers a test condition (e.g., a test compound) is effective against.

In some embodiments, a mixture including a plurality of nucleic acid-tagged cell types is provided and implanted (e.g., by injection, infusion, or other method known in the art) into an animal, e.g., an experimental animal. Methods for creating such xenograft models are known in the art. In some embodiments, the plurality of cell types includes various cancer or tumor cell lines, and the methods can be used to determine whether a given test condition (e.g., one or more test compounds) is active against tumors with different genetic backgrounds, e.g., having different mutation statuses, from different patients, different tissues, or different stages, thereby drastically decreasing time and numbers of animals needed to screen each test condition. Those cells that are present in reduced numbers after exposure to the test conditions can be considered sensitive to the test conditions, while those cells that are present in the same or increased numbers after exposure to the test conditions can be considered resistant or not sensitive to the test conditions.

In some embodiments, the plurality of cell types includes other cell types, e.g., different stem cell types, or non-cancerous cells from various "normal" tissues, and the methods can be used, e.g., to screen test conditions (e.g., test compounds) that affect organ or tissue transplant rejection, e.g., to identify test conditions that improve organ or tissue transplant success, e.g., by reducing rejection rates. Transplantation success of those cells that are present in the same or increased numbers after exposure to the test conditions can be considered improved by the test conditions, while those cells that are present reduced numbers after exposure to the test conditions can be considered not improved to the test conditions.

EXAMPLES

The invention is further described in the following examples, which do not limit the scope of the invention described in the claims.

Example 1. PRISM

To establish feasibility and determine sensitivity of PRISM methods as described herein, five human adenocarcinoma cell lines were stably infected with five different barcode lentiviruses. The lentiviral barcoding vectors were prepared as follows. A 6.4 kb MluI-ClaI fragment was isolated from pLenti6.2/V5DEST (Invitrogen) and ligated to a linker comprising oligonucleotides 5'-CGATAA-CTGCA-GAACCAATGCATTGGA-3' (SEQ ID NO:1) and 5'-CGCGTCCAATGCATTGGTTCTGCAGTTAT-3' (SEQ ID NO:2). A library of MluI-PstI linkers was constructed using 24-bp Luminex DNA barcodes (Peck et al., Genome Biol 7, R61 (2006)) placed within oligonucleotides 5'-CGCGTXXXXXXXXXXXXXXXXXXXXXXXXCT-GCA-3' and 5'-Gxxxxxxxxxxxxxxxxxx-xxxxxxA-3', where XXX . . . XXX includes the sense barcode sequence and xxx . . . xxx includes the antisense barcode sequence, and each of these linkers was individually ligated into the MluI-PstI backbone of the above vector to generate lentiviral barcoding plasmids. Lentivirus was generated from lentivral barcoding plasmids as previously described (addgene.org/static/data/70/82/1619d3c0-af64-11e0-90fe-003048dd6500.pdf) using pCMV-dR8.2 dvpr and pCMV-VSVG packaging vectors in FuGENE6-transfected (Roche Corporation) HEK-293T cells; viral supernatant was collected after 72 h, passed through a sterile 0.45 μm syringe filter (VWR cat. 28144-007), and stored at −80° C.

Cell lines were obtained through the American Type Culture Collection or provided by the Broad-Novartis Cancer Cell Line Encyclopedia (Barretina et al., Nature 483, 603 (Mar. 29, 2012)) and cultured in HEPES-buffered RPMI medium (ATCC cat. 30-2001) containing 10% heat-inactivated fetal bovine serum (Sigma cat. F5410) and penicillin/streptomycin G (Invitrogen cat. 10378-016).

Barcode-containing lentiviruses were used to infect human tumor cell lines at 1:20 dilution with sham-infection controls. The following day, virus was removed and media was replaced by fresh media containing blasticidin (Invitrogen) at a final concentration of 3-10 μg ml-1 media in both virally infected and sham-infected cells. Culture in blasticidin-containing media was continued in infected and sham-infected cells for 2-4 weeks until no sham-infected cells survived. Polybrene was used to increase infection efficiency. Cell lines were considered to be tagged successfully if the untagged cells were dead or almost completely dead through day 14, and the tagged cells remained alive in media with blasticidin. Barcoded lines were frozen in 10% DMSO individually and later frozen as defined pools.

PRISM detection was performed as follows. Genomic DNA from cell lysates was amplified by PCR using primers Biotin pLENTR4 (5'-Biotin-CGTCATTACTAACCGG-TACGC-3'; SEQ ID NO:3) and pLENTF1 (5'-GGAATA-GAAG-AAGAAGGTGG-3'; SEQ ID NO:4). PCR product was hybridized to Luminex beads with covalently attached antisense barcodes, and streptavidin-phycoerythrin addition, washing, and detection on Luminex FlexMap machines was performed as previously described (Peck et al., Genome Biol 7, R61 (2006)). PCR without genomic DNA was hybridized with beads to serve as background control; signal for each bead was subtracted from each sample measurement. DMSO-treated cell mixtures were used as reference control for scaling of each cell line signal at the conclusion of each experiment (viability=100 for each cell line).

Figure 1A:
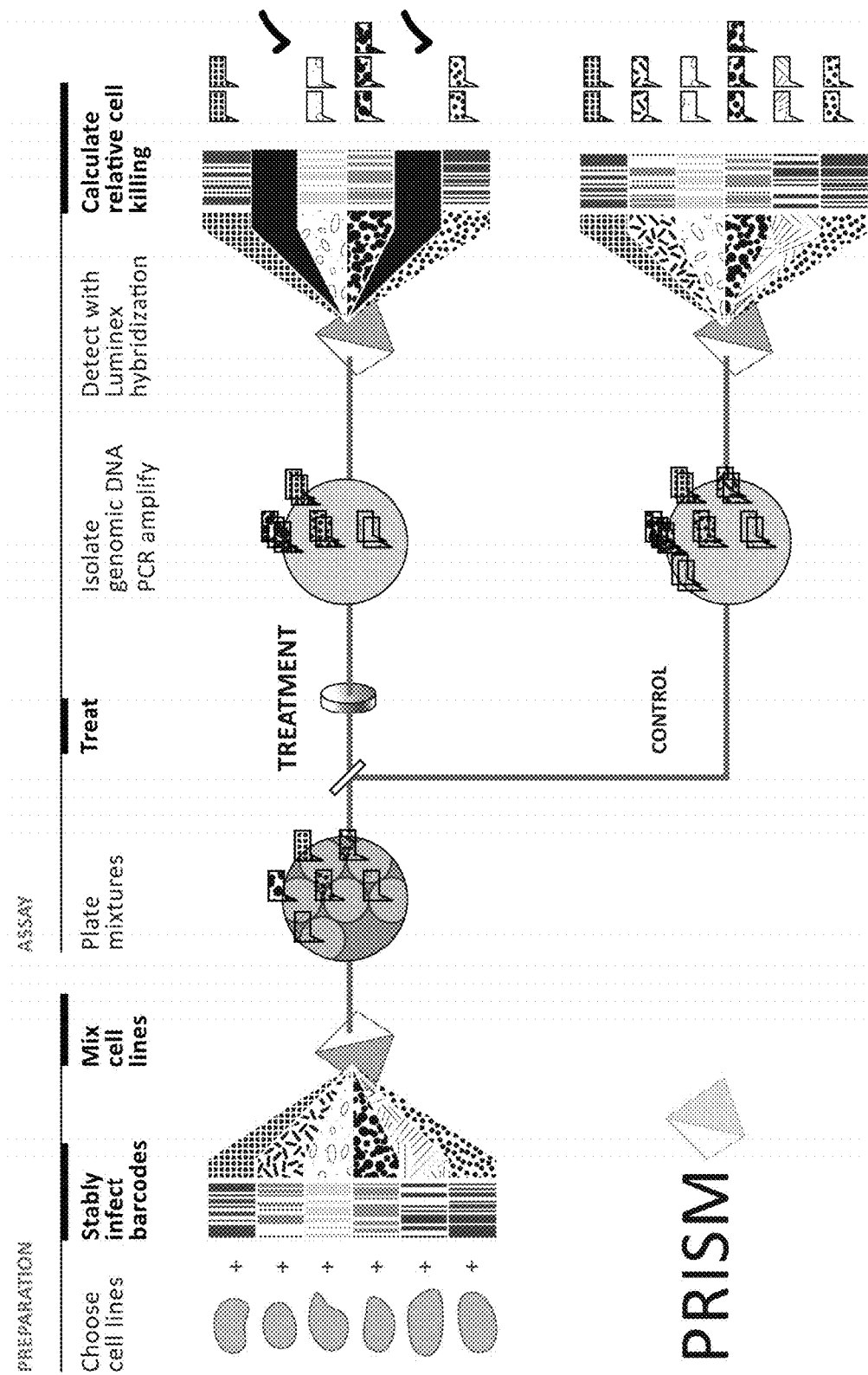
FIG. 1a, Exemplary PRISM method. 24-basepair DNA barcodes encoded within lentiviruses are stably integrated into individual tumor cell lines after blasticidin selection, and barcoded cell lines are individually frozen and later thawed to generate mixtures of equal numbers of barcoded cell lines, which are frozen again. Thawed mixtures are plated and then rearrayed into tissue culture assay plates. Mixtures are treated with test compounds or vehicle (dimethylsulfoxide) controls. At assay conclusion, genomic DNA is harvested from the mixture of remaining viable cells. Barcode sequences are amplified using polymerase chain reaction and universal primers (one of which is biotinylated), and amplified sequences are hybridized to individual microbeads harboring antisense barcode sequences and then to streptavidin-phycoerythrin. A Luminex FlexMap detector quantitates fluorescent signal for each bead. To adjust for differing barcoding efficiencies and differing cell doubling, the signal for each barcoded cell line is scaled to that of vehicle-treated control, thus demonstrating relative inhibition profiles for specific test compounds across multiple cell lines in mixture.
Figure 1B:
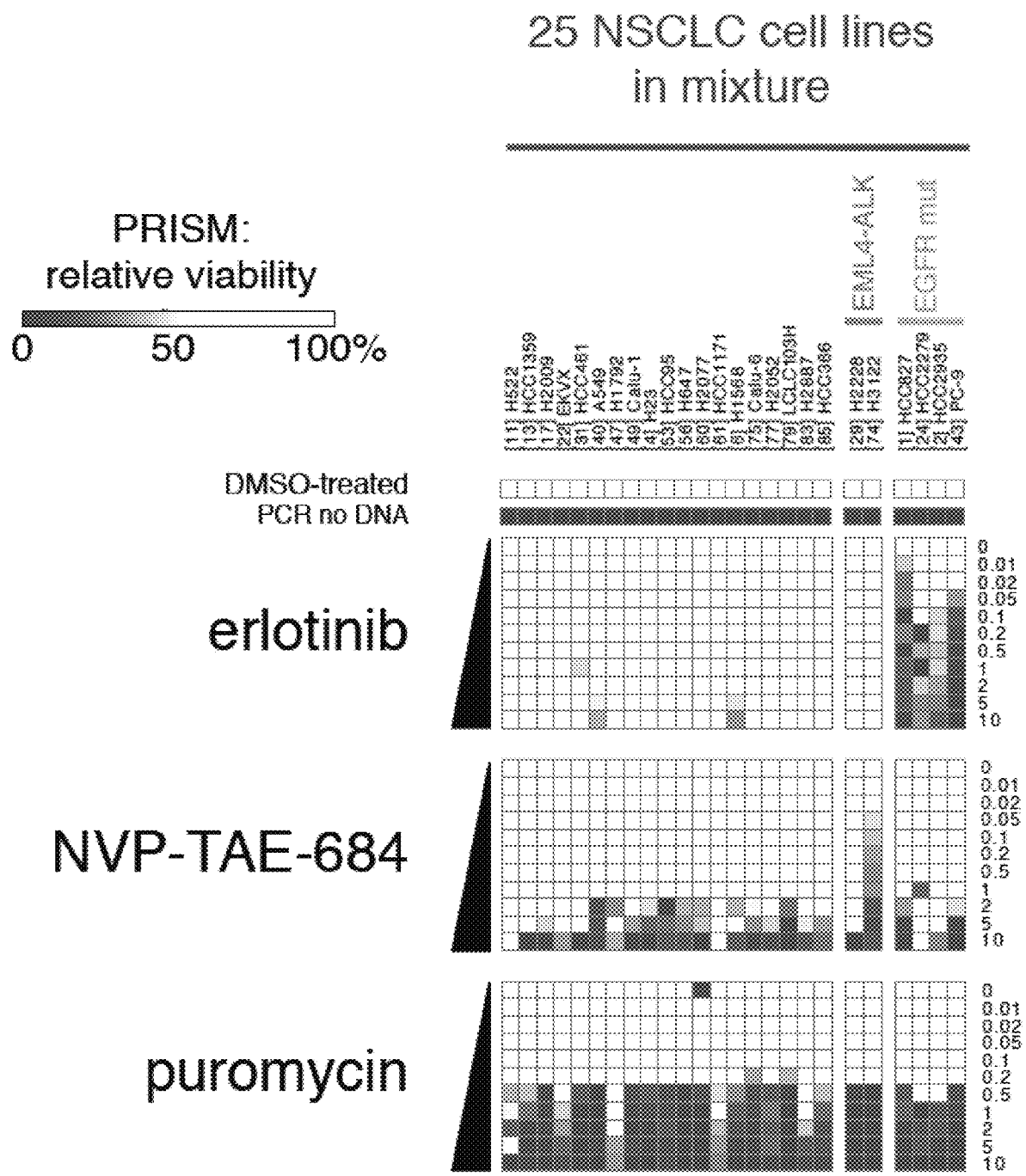
FIG. 1b, Relative inhibition profiles of erlotinib, NVP-TAE-684, and puromycin in a mixture of 25 barcoded lung adenocarcinoma cell lines (non-small cell lung carcinoma, NSCLC) in mixture. Twenty-five barcoded lung adenocarcinoma cell lines were tested in mixture against varying concentrations of the epidermal growth-factor inhibitor erlotinib or the anaplastic lymphoma kinase inhibitor NVP-TAE-684 (at 0-10 μM) or the ribosomal inhibitor puromycin (at 0-10 μg/ml) and viability relative to DMSO-treated control is plotted as a color gradient. Cell lines are listed with bracketed barcode numbers. EML4-ALK, cell lines containing EML4-ALK translocations; EGFR mut, cell lines containing EGFR mutations; PCR no DNA, background bead signals from PCR reactions without genomic DNA template. See text for details.
Figure 1C:
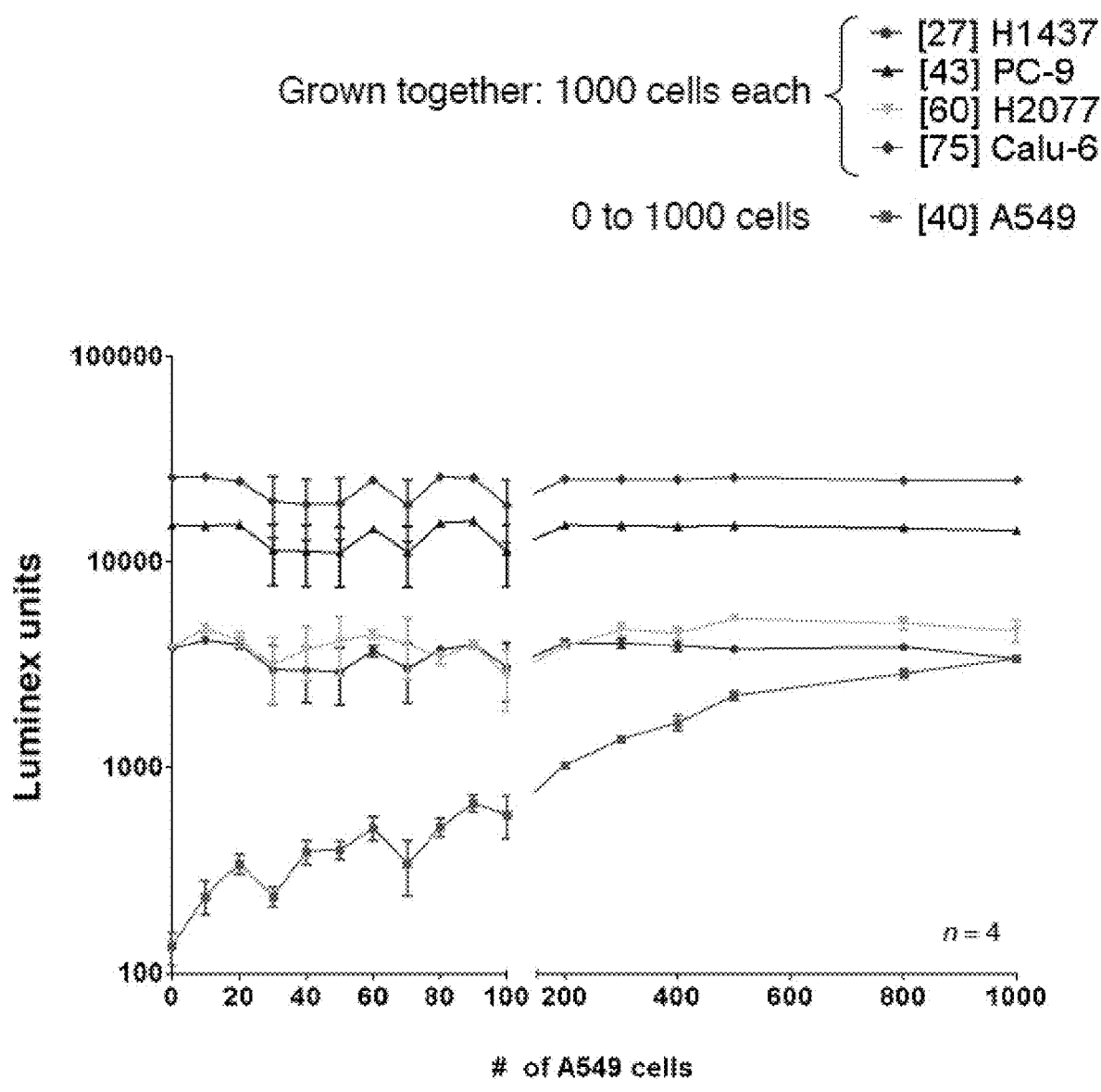
FIG. 1c. Five human lung adenocarcinoma cell lines (H1437, PC-9, H2077, Calu-6, and A549) were labeled with a lentivirus encoding a specific 24-basepair sequence (the specific sequence number is designated within brackets in the cell line name) and expression of the bsd blasticidin-resistance gene; each cell line was selected for blasticidin resistance. Designated numbers of cells were plated together in mixture in a well of a 96-well tissue culture plate. The following day, genomic DNA was prepared from cell mixtures, and polymerase chain reaction-amplified barcodes were hybridized to microbeads corresponding to each barcode; quantitative fluorescent signals were read on a Luminex FlexMap detector. The fluorescent signal for barcoded A549 cells (mean± standard error of the mean) is directly proportional to the number of cells.

FIG. 1c shows fluorescent signals of each barcode: the four invariant lines show similar signals in all mixtures, while the varied fifth line shows signal which is directly proportional to cell number. Thus, the assay was highly sensitive, with the ability to detect as few as 10 cells in a mixture of 4000 cells (representing fewer than 0.5% of the total cell number).

To examine differential responses of cells in mixture to exogenous compounds within a single cancer type—an approach which could highlight important genetic vulnerabilities in subclasses of the same cancer—25 human lung adenocarcinoma cell lines were chosen that have doubling times of 0.5-1.5 days (hence several doublings in a 5-day assay) and grow in RPMI media supplemented with 10% fetal bovine serum. These lines were barcoded as described above, and equal numbers of cells of each cell lines were mixed together. Cell mixtures were plated in 384-well plates on day −1. On day 0, mixtures were challenged with compounds or vehicle, and on day 5 genomic DNA was harvested and barcodes quantitated. Barcode signal background was determined using beads hybridizing to PCR reactions lacking genomic DNA templates and was subtracted from all measurements. To account for different doubling times of cell lines and different baseline signals for each cell line, the barcode signal for each cell line was scaled to the signal of the vehicle-treated control at the end of the experiment (PRISM schema shown in FIG. 1A), so that the relative growth inhibition of each cell line was assessed.

Treatment with vehicle alone resulted in no growth inhibition, and treatment with puromycin resulted in uniform cell death across the cell line mixture, as expected. In contrast, FIG. 1B illustrates selective and dose-dependent decrease of four EGFR-mutant cell lines in the mixture (HCC827, HCC2279, HCC2935, and PC-9) by EGFR inhibitor erlotinib (concordant with previous studies performed in individual cell lines (Sos et al., J Clin Invest 119, 1727-1740 (2009). The expected pattern of cell killing with the ALK kinase inhibitor NVP-TAE-684 was observed (FIG. 1B). Two cell lines in the mixture harbor ALK-activating chromosomal translocations involving EML4 and ALK, including the H3122 cell line, which is reported to be sensitive to the ALK inhibitor (Koivunen et al., Clin Cancer Res 14, 4275-4283 (2008)). Indeed, selective killing was observed of H3122, but not H2228, which is known to be NVP-TAE-684 resistant (Koivunen et al., Clin Cancer Res 14, 4275-4283 (2008)). These experiments establish the feasibility of PRISM to precisely recapitulate expected patterns of drug sensitivity and resistance amid a mixture of lung cancer cell lines.

To investigate cancer vulnerabilities that are common in multiple cancer types and to examine the extent to which assaying cells in mixture may be complicated by cell-cell interactions, a panel of 100 barcoded cell lines was created comprising 18 different cancer types, and these were challenged in mixture with each of 43 anticancer compounds (including both targeted and general cytotoxic agents) in 8-point dose response. Each compound was represented by 3,200 functional measurements (100 cell lines×8 doses×4 replicates). The assays were performed as follows. Frozen mixtures of barcoded cell lines were thawed (day −2) and replated (day −1) into 384-well microtiter plates. On day 0, compounds suspended in DMSO were pinned into cultures to achieve final concentrations of 0.0012, 0.0049, 0.019, 0.078, 0.3125, 1.25, 5, or 20 μg ml-1. On day 5, cells were washed with phosphate-buffered saline and lysed for 60 minutes at 60° C. in 20 mM Tris-HCl (pH 8.4), 50 mM KCl, 0.45% IGEPAL CA-630 (Sigma cat. 18896), 0.45% Tween-20 (Sigma cat. P9416), and 10% proteinase K (Qiagen cat. 19133). Proteinase K was inactivated by a 15-minute incubation at 95° C.

PRISM detection was performed as described above. As expected, PRISM revealed similar patterns of cytotoxic activity among functionally related compounds (e.g., microtubule binders, topoisomerase inhibitors, or MEK kinase inhibitors) (FIG. 3C).

To quantitatively compare the 100-cell line PRISM performance to traditional methods, PRISM was compared to the activity of 23 compounds across the same 100 cell lines grown individually, as recently reported (using either ATP content measurements using the CellTiterGlo (CTG), or direct enumeration of cell nuclei using an optical fluorescent imaging method (PerkinElmer Opera system (hereafter, OPTICAL)) and thus served as a gold standard against which PRISM could be compared (Barretina et al., Nature 483, 603 (Mar. 29, 2012)). The same parental cell lines were used in all three methods; in the PRISM method, a barcoded "daughter" line was generated from the common parental cell line. Compounds used in assays were replica-plated from the same source. The cell lines grown individually were assayed at day 3 following compound treatment, whereas the 100-cell line PRISM mixture was analyzed at day 5.

Figure 2A:
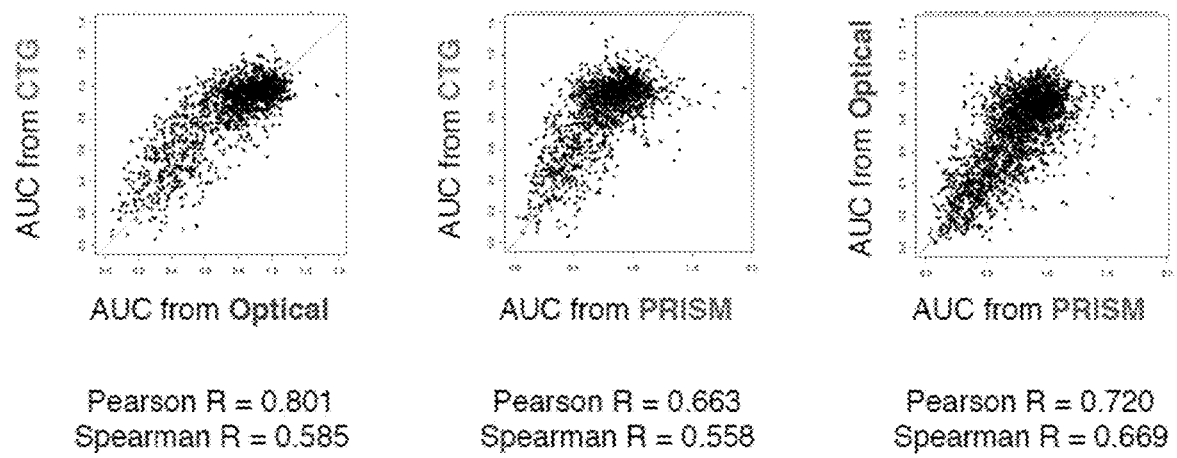
FIG. 2a, Area under the curve comparisons of cell viability measures with PRISM. Three methods (CTG, Promega CellTiterGlo measurement of adenosine triphosphate; OPTICAL, PerkinElmer Opera system enumeration of fluorescent-staining nuclei; and PRISM, quantitation of DNA barcodes) were used to determine cell viability after subjecting 100 human cancer cell lines (representing 18 tissues of origin) either individually (CTG, OPTICAL) or in mixture (PRISM) to 23 antitumor compounds at 8 concentrations. The AUC (Area Under the Curve) for the viability vs. log(concentration), ranging from 0 to 1, was determined for each cell line-compound combination for each method, and pairwise correlations between the methods are shown.
Figure 2B:
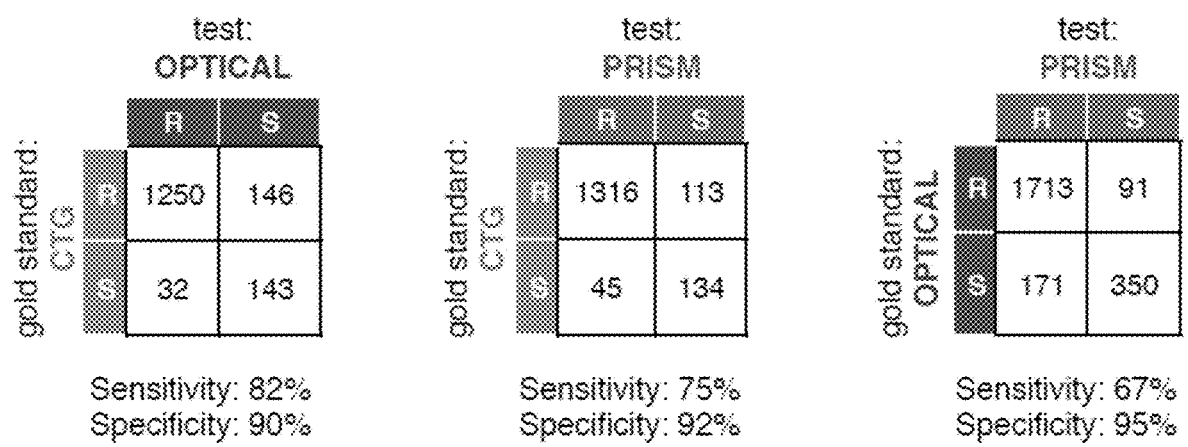
FIG. 2b, Comparison of predictions of drug sensitivity using different cell viability measures. CTG, OPTICAL, and PRISM methods were compared for their ability to predict drug sensitivity (shown here with choice of AUC<0.5) for individual cell lines.
Figure 2C:
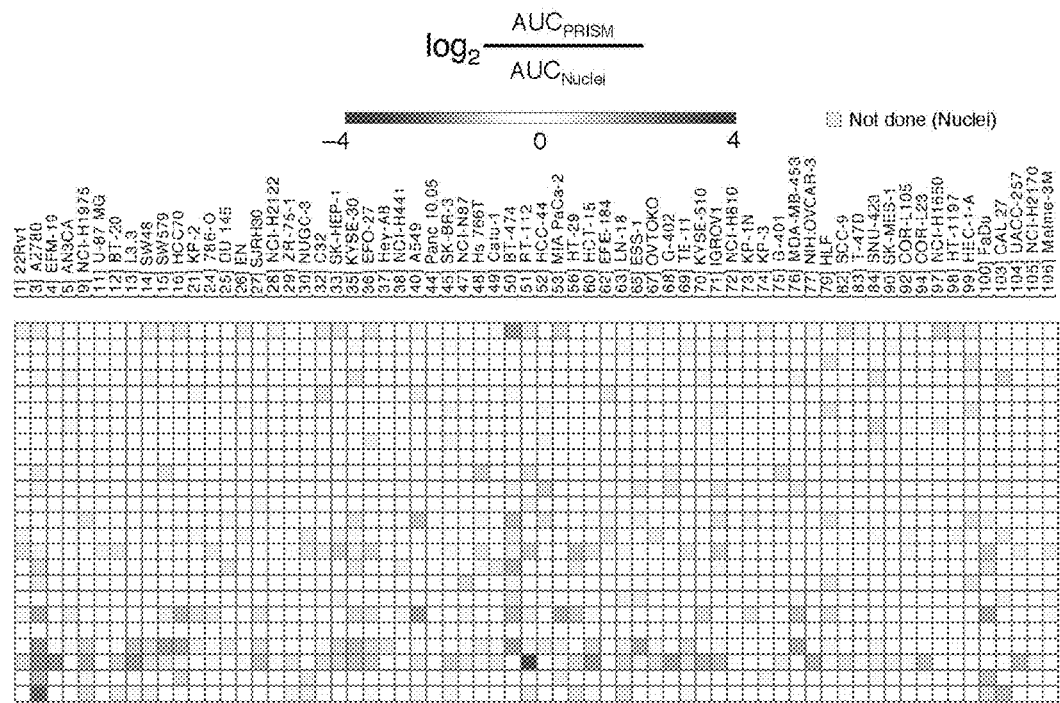
FIGS. 2c-d, Outlier analysis of discrepancies between PRISM and other cell viability measurements. The $\log_2$ of the ratio of the AUC measured by PRISM to the AUC measured by either OPTICAL (c) or CTG (d) was used to determine whether specific cell lines or compounds were enriched for discrepancies between PRISM and other cell viability measurements. Yellow shading denotes assays which were not performed in OPTICAL or CTG. See text for details.
Figure 2D:
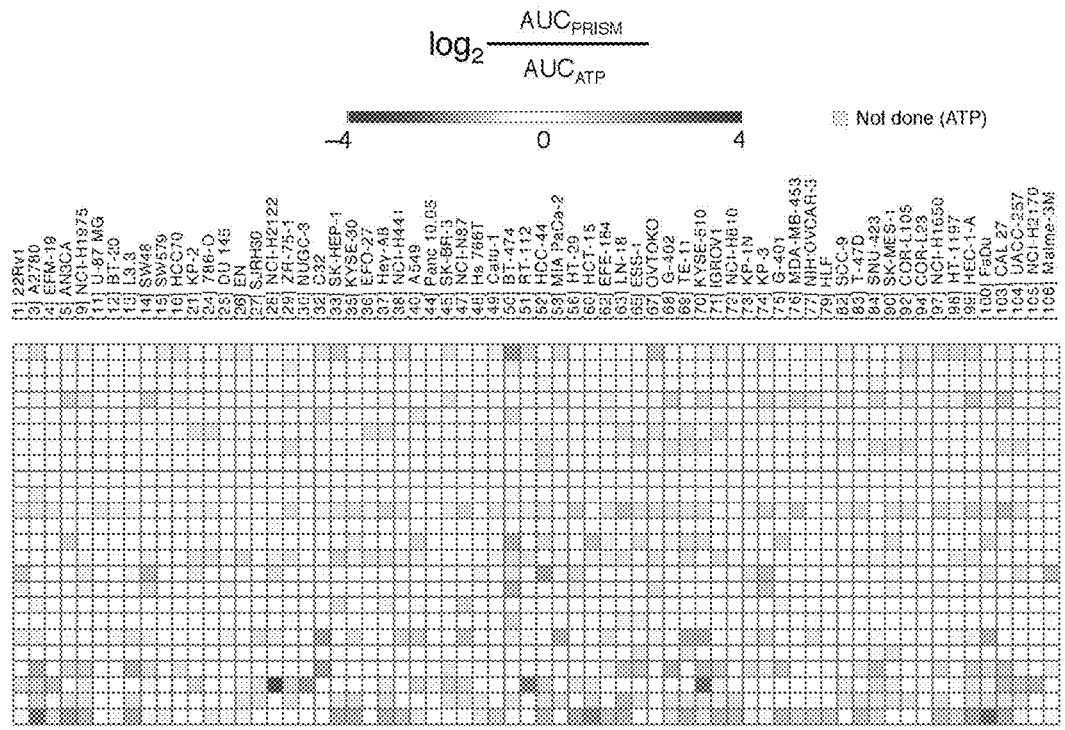

To compare the three methods for measuring cell viability, the AUC (Area Under the Curve, measured from the viability vs. logarithm of drug concentration curve) was calculated for each combination of compound and cell line and for each viability measurement method. The CTG and OPTICAL methods were generally correlated with Pearson R=0.801. CTG and PRISM correlated with R=0.663, and OPTICAL and PRISM correlated with R=0.720. To compare the predictive ability of the three measurements of cell viability globally, AUC of 0.5 was arbitrarily chosen as a threshold to categorize a particular cell line as either sensitive (AUC<0.5) or resistant (AUC≥0.5) to a particular compound, for all three methods (CTG, OPTICAL, PRISM). Designating CTG as a gold standard, OPTICAL demonstrated a sensitivity of 82% and a specificity of 90% (FIG. 2b). With CTG as gold standard, PRISM demonstrated a sensitivity of 75% and specificity of 92%. With OPTICAL as gold standard, PRISM demonstrated a sensitivity of 67% and specificity of 95%. To investigate whether particular cell lines or specific compounds were disproportionately responsible for divergent predictive results between PRISM and the other methods, we examined the ratio between PRISM AUC and OPTICAL AUC (FIG. 2c) or PRISM AUC and OPTICAL AUC (FIG. 2d). The most divergent AUC measurements (i.e., with the most intense color in the figure) were generally not associated with any particular cell line or compound, with the possible exceptions of paclitaxel, which showed higher AUC in PRISM than in OPTICAL in many cell lines (FIG. 2c), and topotecan, which showed lower AUC in PRISM than in CTG (FIG. 2d). In these rare cases, either the different assay conditions (5-day assay with PRISM, 3-day assay with OPTICAL and CTG) or the assay of cells in mixture might explain the discrepancy. Overall, however, PRISM appears to perform comparably to these other methods in global determinations of sensitivity to compounds in these 100 cell lines.

Next several oncogene mutations previously shown to predict response to individual compounds were examined. Oncogene mutations in the BRAF or EGFR genes were determined previously for 100 cell lines and used to stratify responses to compounds. PRISM, OPTICAL, and CTG demonstrated significant (two-tailed t-test, $p<0.05$) reductions in cell viability with the BRAF inhibitor PLX4720 in BRAF V600E mutant lines compared to BRAF wild-type lines (FIG. 3a); a similar reduction was seen only with PRISM with the RAF inhibitor RAF-265 (FIG. 3a) but not with the RAF inhibitor sorafenib (FIG. 3a). Meanwhile, presumably acting downstream of RAF, the MEK inhibitor AZD6244 demonstrated significant reduction in BRAF V600E mutant lines compared to BRAF wild-type lines with CTG but only a trend towards this reduction in both PRISM and OPTICAL (FIG. 3a). Cell lines containing activating EGFR mutations without secondary "gatekeeper" mutations displayed a trend towards increased sensitivity to erlotinib (FIG. 3b) but this did not reach statistical significance with any method, possibly due to the small number of EGFR-mutant lines in this collection of 100 cell lines.

The ability of PRISM to display functional similarities between compounds that share the same target was evaluated. Using the 28 aforementioned compounds and 15 additional chemotherapeutic compounds we performed hierarchical clustering of the PRISM cell viability responses to determine similarities in compound actions. n this experiment, each compound was represented by 3200 functional measurements (=100 cell lines×8 compound doses×4 replicates). FIG. 3c illustrates the functional relatedness of compounds of different targets using this 100-cell line "chemofingerprinting" panel.

Example 2. PRISM In Vivo

To extend PRISM to use in animal xenograft models of cancer, a mixture of 24 barcoded human lung adenocarcinoma cell lines ($10^6$ cells per line) was injected subcutaneously into NSG (NOD scid IL2Rgamma$^{null}$) mice (FIG. 4a). Following the appearance of palpable tumors (~1 cm diameter), beginning 12 days following injection of the cell lines, mice were treated with oral gavage using either the EGFR inhibitor erlotinib (50 mg/kg body weight) or vehicle control (1% sodium carboxymethyl cellulose), (n=10 mice in each group). After several weeks, mice were sacrificed and tumors excised. Tumors were sectioned into 4-5 adjacent fractions, genomic DNA was harvested, and the relative abundance of each cell line in each portion was determined by PRISM: for each sample, the fluorescent signal for each cell line was converted to cell number using the signal from the cell mixture used for injection, and these cell numbers were used to calculate the relative contribution of each cell line to the tumor.

In vehicle-treated mice (FIG. 4b), 23 out of 24 cell lines were detectable at tumor harvest in 10 of 10 mice. Of particular interest, while the 23 detectable lines grew at different rates, their relative abundances within the tumor were nearly identical in each of the 10 vehicle-treated xenografts (FIG. 4c). Similarly, four different portions of each tumor were sampled, and there was little variation in the contribution of particular cells in different parts of the tumor.

Next, it was asked whether PRISM could be used to detect genotype-specific drug sensitivity in vivo. To test this, a cohort of 20 mice injected with the 24-cell line pool was treated once daily for 16 days by gavage with either the EGFR inhibitor erlotinib (50 mg/kg body weight, n=10 mice) or vehicle control (1% sodium carboxymethyl cellulose, n=10), beginning 12 days following injection of the cell lines. The tumors were than resected, and the abundance of each cell line measured by PRISM. Erlotinib treatment (FIG. 4c) caused a marked relative reduction in all 4 EGFR-mutant lines by 22%, 88%, 75%, and 76%, while the detectable 19 wt-EGFR lines were mostly unchanged or increased in representation; the 4 wt-EGFR lines which decreased in representation were relatively decreased by 5%, 19%, 21%, and 41%. HCC2935, the EGFR-mutant line which did not show significant change with erlotinib treatment, was previously found of the 4 mutant lines to be the least sensitive to erlotinib in vitro (FIG. 1b). Across all 20 mice, the median coefficient of variation for individual cell lines was 11.4%. Overall, not only were nearly all lines precisely detectable in this experiment, but known sensitivities were also recovered despite the complex mixture of coexisting tumor cell lines in vivo. These experiments attest to the feasibility of PRISM to accurately assess drug sensitivity in both the in vitro and in vivo settings.

Thus, the PRISM method efficiently elucidates phenotypic responses in cellular models of cancer: using stably integrated DNA barcode sequences, simultaneous assay of multiple cell lines can be performed in the same well of a tissue culture plate or in the same tumor of a mouse. Unlike other barcoding approaches used in cancer cells, PRISM utilizes the barcode solely as a unique and quantifiable marker for cell number and not as a marker of a specific genetic alteration. Converting barcode signal to cell number using measured baseline or control relationships permits the barcode to thus be used as a surrogate for cell number in experiments using mixtures of cell line models.

Example 3. Using PRISM to Identify Novel Anticancer Compounds

PRISM was used to identify novel anticancer compounds, using a set of 102 barcoded cell lines including 90 non-small cell lung adenocarcinoma lines (and 2 duplicate lines with different barcode labels) and 10 remaining cell lines representing other tissues of origins. These were assayed in pools against a library of 8,000 novel small molecules created using combinatorial methods of Diversity-Oriented Synthesis (DOS) (Comer et al., Proc Natl Acad Sci USA 108, 6751 (Apr. 26, 2011; Lowe et al., J Org Chem 77, 7187 (Sep. 7, 2012); Marcaurelle et al., J Am Chem Soc 132, 16962 (Dec. 1, 2010))—to investigate chemical compounds not represented in traditional pharmaceutical libraries—and ~200 tool compounds previously demonstrated to have activity in cancer cell lines (Schreiber et al., Nat Biotechnol 28, 904 (September, 2010)). Of the 8,000 DOS compounds tested in duplicate at a single 16.6 µM dose, 199/8000 (2.5%) demonstrated significant activity in PRISM, i.e., reducing the viability of at least one of the 102 cell lines to 20% of that of its vehicle-treated counterpart. One hundred of these compounds demonstrated activity in a PRISM validation assay across 8 doses.

Example 4. PRISM Identifies BRD-7880, an Aurora Kinase Inhibitor

One compound identified using the methods in Example 3, BRD-7880 (FIG. 5a), demonstrated both marked selectivity (with AUC<0.5 in 12 of 102 cell lines) and potency (average EC50~1 µM) in PRISM (FIG. 5b). Using the AUC for each cell line's response to BRD-7880, a PRISM "activity profile" was created to query whether the sensitivity pattern of BRD-7880 across the cell line panel was related to any of the tool compounds assayed in parallel. BRD-7880 showed strikingly similar activity to the aurora kinase inhibitor tozasertib (VX-680) (Spearman $r^2$=0.68, FIG. 5c). Thus it was hypothesized that BRD-7880 was functioning as an inhibitor of aurora kinases.

In vitro kinase inhibition assays were then performed as follows. Incorporation of radioactivity from 10 µM γ-$^{33}$P-ATP was measured across 8 doses in duplicate by the EMD Millipore KinaseProfiler service (Billerica, Mass.) under published standard conditions with 10 mM ATP. Full-length human aurora-A was assayed with 200 µM LRRASLG (Kemptide); full-length human aurora-B with 30 µM AKRRRLSSLRA (SEQ ID NO:5); and full-length human aurora-C with 30 µM AKRRRLSSLRA (SEQ ID NO:6). IC50 values were modeled using least-squares and variable slope with Prism 6.0 software (GraphPad, San Diego, Calif.).

The results of the in vitro kinase activity assays verified that BRD-7880 is a selective inhibitor of aurora kinase B and C (IC50 of 7 nM and 12 nM, respectively) and a weaker inhibitor of aurora kinase A (IC50 2153 nM) (FIG. 5d). In vitro kinase activity profiling across 308 kinases using the Millipore KinaseProfiler assay demonstrated highly selective significant inhibition (defined as activity<25% control) by BRD-7880, which inhibited aurora kinase B (FIG. 5e), compared to less selective inhibition by tozasertib, which inhibited aurora kinases A, B, and C, in addition to several other kinases (FIG. 5f). A screen of binding selectivity across 98 kinases (DiscoveRx scanEDGE panel, with the addition of aurora kinase C) using the DiscoveRx KinomeScan method, demonstrated that BRD-7880 showed the most significant binding to aurora kinase B and aurora kinase C (0.5% and 3% of control, respectively), with less binding to aurora kinase A (25% of control). The results of the KinomeScan are shown in Table 1, below.

Treatment of HCT-116 cells resulted in polyploidy and decreased phosphorylation of serine 10 in histone H3 as observed previously with other inhibitors of aurora kinase B (Andrews et al., Curr Opin Cell Biol 15, 672 (December, 2003); Carmena and Earnshaw, Nat Rev Mol Cell Biol 4, 842 (November, 2003); Ditchfield et al., J Cell Biol 161, 267 (Apr. 28, 2003)).

In addition, HCT-116 cells were treated with 10 µM of DMSO, or the Aurora Kinase Inhibitors barasertib, GSK1070916, MLN8054, BRD-7880, or tozasertib. 24 hours or 48 hours following treatment, cells were stained with propidium iodide and DNA content per cell was assessed using a Becton Dickinson LSR II flow cytometer. As shown in FIG. 5g, BRD-7880 and the other aurora kinase inhibitors increased DNA content of HCT-116 cells.

Finally, HCT-116 cells were treated with 10 µM of DMSO, barasertib, GSK1070916, MLN8054, BRD-7880, or tozasertib. Cells lysates were probed on Western blot using antibodies (diluted 1:1000) to histone H3 (Abcam cat. no. 24834), phosphoserine 10-histone H3 (Cell Signaling Technology cat no. 3377SS), aurora kinase B (Millipore cat. no. 04-1036), or beta-actin (Santa Cruz Biotechnology cat. no. sc-47778) and detected using a LI-COR Odyssey analyzer. As shown in FIG. 5h, BRD-7880 and other aurora kinase inhibitors decrease phosphorylation of serine 10 on histone H3, a marker of aurora B kinase activity.

By enabling simultaneous activity profiling across multiple cell lines, PRISM facilitated here the rapid identification of a target of a specific, potent, novel small molecule inhibitor of cancer cell lines.

TABLE 1

| KINOMEscan Gene Symbol | Entrez Gene Symbol | Percent Control |
|---|---|---|
| ABL1(E255K)---phosphorylated | ABL1 | 80 |
| ABL1(T315I)---phosphorylated | ABL1 | 44 |
| ABL1---nonphosphorylated | ABL1 | 100 |
| ABL1---phosphorylated | ABL1 | 88 |
| ACVR1B | ACVR1B | 84 |
| ADCK3 | CABC1 | 84 |
| AKT1 | AKT1 | 87 |
| AKT2 | AKT2 | 80 |
| ALK | ALK | 100 |
| AURKA | AURKA | 22 |
| AURKB | AURKB | 0.5 |
| AURKC | AURKC | 3 |
| AXL | AXL | 84 |
| BMPR2 | BMPR2 | 100 |
| BRAF | BRAF | 70 |
| BRAF(V600E) | BRAF | 65 |
| BTK | BTK | 94 |
| CDK11 | CDK19 | 43 |
| CDK2 | CDK2 | 100 |
| CDK3 | CDK3 | 76 |
| CDK7 | CDK7 | 77 |
| CDK9 | CDK9 | 90 |
| CHEK1 | CHEK1 | 100 |
| CSF1R | CSF1R | 100 |
| CSNK1D | CSNK1D | 100 |
| CSNK1G2 | CSNK1G2 | 100 |
| DCAMKL1 | DCLK1 | 37 |
| DYRK1B | DYRK1B | 55 |
| EGFR | EGFR | 66 |
| EGFR(L858R) | EGFR | 60 |
| EPHA2 | EPHA2 | 86 |
| ERBB2 | ERBB2 | 100 |
| ERBB4 | ERBB4 | 97 |
| ERK1 | MAPK3 | 92 |
| FAK | PTK2 | 100 |
| FGFR2 | FGFR2 | 77 |
| FGFR3 | FGFR3 | 56 |
| FLT3 | FLT3 | 65 |
| GSK3B | GSK3B | 94 |
| IGF1R | IGF1R | 88 |
| IKK---alpha | CHUK | 58 |
| IKK---beta | IKBKB | 68 |
| INSR | INSR | 36 |
| JAK2(JH1domain---catalytic) | JAK2 | 98 |
| JAK3(JH1domain---catalytic) | JAK3 | 66 |
| JNK1 | MAPK8 | 91 |
| JNK2 | MAPK9 | 89 |
| JNK3 | MAPK10 | 70 |
| KIT | KIT | 77 |
| KIT(D816V) | KIT | 72 |
| KIT(V559D,T670I) | KIT | 100 |
| LKB1 | STK11 | 39 |
| MAP3K4 | MAP3K4 | 86 |
| MAPKAPK2 | MAPKAPK2 | 80 |
| MARK3 | MARK3 | 100 |
| MEK1 | MAP2K1 | 71 |
| MEK2 | MAP2K2 | 73 |
| MET | MET | 100 |
| MKNK1 | MKNK1 | 87 |
| MKNK2 | MKNK2 | 77 |
| MLK1 | MAP3K9 | 91 |
| p38---alpha | MAPK14 | 93 |
| p38---beta | MAPK11 | 87 |
| PAK1 | PAK1 | 77 |
| PAK2 | PAK2 | 69 |
| PAK4 | PAK4 | 100 |
| PCTK1 | CDK16 | 95 |
| PDGFRA | PDGFRA | 90 |
| PDGFRB | PDGFRB | 100 |
| PDPK1 | PDPK1 | 48 |
| PIK3C2B | PIK3C2B | 96 |
| PIK3CA | PIK3CA | 74 |

TABLE 1-continued

| KINOMEscan Gene Symbol | Entrez Gene Symbol | Percent Control |
|---|---|---|
| PIK3CG | PIK3CG | 100 |
| PIM1 | PIM1 | 87 |
| PIM2 | PIM2 | 85 |
| PIM3 | PIM3 | 72 |
| PKAC---alpha | PRKACA | 69 |
| PLK1 | PLK1 | 39 |
| PLK3 | PLK3 | 48 |
| PLK4 | PLK4 | 61 |
| PRKCE | PRKCE | 100 |
| RAF1 | RAF1 | 100 |
| RET | RET | 100 |
| RIOK2 | RIOK2 | 38 |
| ROCK2 | ROCK2 | 100 |
| RSK2(Kin.Dom.1---N---terminal) | RPS6KA3 | 80 |
| SNARK | NUAK2 | 72 |
| SRC | SRC | 81 |
| SRPK3 | SRPK3 | 100 |
| TGFBR1 | TGFBR1 | 100 |
| TIE2 | TEK | 97 |
| TRKA | NTRK1 | 84 |
| TSSK1B | TSSK1B | 57 |
| TYK2(JH1domain---catalytic) | TYK2 | 87 |
| ULK2 | ULK2 | 100 |
| VEGFR2 | KDR | 100 |
| YANK3 | STK32C | 91 |
| ZAP70 | ZAP70 | 93 |

Example 5. PRISM Quantification of Barcoded Tumor Cell Lines with Luminex Bead Hybridization vs. Sequencing Mixtures of the 102 barcoded tumor cell lines described in Example 3 were treated with DMSO vehicle for 5 days in culture in microtiter plates. Genomic DNA was prepared from mixtures and relative barcode number was enumerated using either Luminex bead hybridization or sequencing (n=4 each sample). With Luminex bead hybridization, common primers (including one biotinylated primer) were used to amplify barcode sequences by PCR, and hybridization to Luminex xMAP beads covalently attached to antisense barcode was used to quantitate relative numbers of barcodes. With sequencing, similar common primers with additional 5' barcode sequences pertaining to well position were used to amplify barcode sequences by PCR, and sequencing of PCR products using an IonTorrent Personal Genome Machine sequencer with an Ion 318 chip was used to quantitate relative numbers of barcodes.

As shown in FIG. 7, the two methods demonstrate similar relative numbers of barcodes (Spearman r=0.95). Thus there was a correlation between results obtained with Luminex vs. sequencing.

REFERENCES AND NOTES

1. U. McDermott et al., Identification of genotype-correlated sensitivity to selective kinase inhibitors by using high-throughput tumor cell line profiling. *Proc Natl Acad Sci USA* 104, 19936 (Dec. 11, 2007).
2. M. L. Sos et al., Predicting drug susceptibility of non-small cell lung cancers based on genetic lesions. *J Clin Invest* 119, 1727 (June, 2009).
3. J. Barretina et al., The Cancer Cell Line Encyclopedia enables predictive modelling of anticancer drug sensitivity. *Nature* 483, 603 (Mar. 29, 2012).
4. M. J. Garnett et al., Systematic identification of genomic markers of drug sensitivity in cancer cells. *Nature* 483, 570 (Mar. 29, 2012).

5. N. C. Turner, J. S. Reis-Filho, Genetic heterogeneity and cancer drug resistance. *Lancet Oncol* 13, e178 (April, 2012).
6. N. Yamamoto et al., Color coding cancer cells with fluorescent proteins to visualize in vivo cellular interaction in metastatic colonies. *Anticancer Res* 24, 4067 (November-December, 2004).
7. D. Peck et al., A method for high-throughput gene expression signature analysis. *Genome Biol* 7, R61 (2006).
8. M. K. Muellner et al., A chemical-genetic screen reveals a mechanism of resistance to PI3K inhibitors in cancer. *Nat Chem Biol* 7, 787 (November, 2011).
9. J. P. Koivunen et al., EML4-ALK fusion gene and efficacy of an ALK kinase inhibitor in lung cancer. *Clin Cancer Res* 14, 4275 (Jul. 1, 2008).
10. S. M. Wilhelm et al., Preclinical overview of sorafenib, a multikinase inhibitor that targets both Raf and VEGF and PDGF receptor tyrosine kinase signaling. *Mol Cancer Ther* 7, 3129 (October, 2008).
11. K. T. Flaherty et al., Improved survival with MEK inhibition in BRAF-mutated melanoma. *N Engl J Med* 367, 107 (Jul. 12, 2012).
12. E. Comer et al., Fragment-based domain shuffling approach for the synthesis of pyran-based macrocycles. *Proc Natl Acad Sci USA* 108, 6751 (Apr. 26, 2011).
13. J. T. Lowe et al., Synthesis and profiling of a diverse collection of azetidine-based scaffolds for the development of CNS-focused lead-like libraries. *J Org Chem* 77, 7187 (Sep. 7, 2012).
14. L. A. Marcaurelle et al., An aldol-based build/couple/pair strategy for the synthesis of medium- and large-sized rings: discovery of macrocyclic histone deacetylase inhibitors. *J Am Chem Soc* 132, 16962 (Dec. 1, 2010).
15. S. L. Schreiber et al., Towards patient-based cancer therapeutics. *Nat Biotechnol* 28, 904 (September, 2010).
16. P. D. Andrews, E. Knatko, W. J. Moore, J. R. Swedlow, Mitotic mechanics: the auroras come into view. *Curr Opin Cell Biol* 15, 672 (December, 2003).
17. M. Carmena, W. C. Earnshaw, The cellular geography of aurora kinases. *Nat Rev Mol Cell Biol* 4, 842 (November, 2003).
18. C. Ditchfield et al., Aurora B couples chromosome alignment with anaphase by targeting BubR1, Mad2, and Cenp-E to kinetochores. *J Cell Biol* 161, 267 (Apr. 28, 2003).
19. addgene.org/static/data/70/82/1619d3c0-af64-11e0-90fe-003048dd6500.pdf.

OTHER EMBODIMENTS

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:

1. A method for simultaneously determining the effect of a test condition on viability or proliferation of the cells of each of a plurality of different genetically heterogeneous mammalian cell types, the method comprising:
(a) providing a unitary population of cells comprising a plurality of different genetically heterogeneous mammalian cell types, wherein the cells of each of the cell types of the unitary population of cells are known and each cell in each of the cell types of the unitary population of cells further comprises:
(i) an exogenous nucleic acid tag stably integrated into the genome of said cell in each of the cell types, comprising a core sequence that is unique to one of the cell types, and flanking amplification primer binding sequences that are the same in all cells of the plurality of different genetically heterogeneous mammalian cell types, and
(ii) optionally a selectable or detectable marker;
and forming a first sample and a second sample by splitting the unitary population of cells, wherein the first sample and the second sample contain the same amount of the unitary population of cells;
(b) exposing the first sample, but not exposing the second sample, to a test condition for a selected time,
wherein said exposing the first sample to a test condition comprises contacting the first sample with a test compound or altering an environmental condition affecting the first sample;
(c) growing the cells of the first sample and the cells of the second sample in the same condition for a period of time after the cells of the first sample are exposed to the test condition;
(d) detecting a relative level of the exogenous nucleic acid tag of each of the cell types of the unitary population of cells in the first sample and detecting a relative level of the exogenous nucleic acid of each of the cell types of the unitary population of cells in the second sample after step (c), wherein the relative level of the exogenous nucleic acid tag of each of the cell types of the unitary population of cells in the first sample is proportional to the number of cells of each of the cell types of the unitary population of cells in the first sample after said exposing the first sample to a test condition for a selected time and the relative level of the exogenous nucleic acid tag of each of the cell types of the unitary population of cells in the second sample is proportional to the number of cells of each of the cell types of the unitary population of cells in the second sample after said not exposing the second sample to the test condition for the selected time, wherein said detecting a relative level of the exogenous nucleic acid tag of each of the cell types of the unitary population of cells in the first sample and said detecting a relative level of the exogenous nucleic acid of each of the cell types of the unitary population of cells in the second sample comprises producing a plurality of different amplified nucleic acid tags by amplifying the exogenous nucleic acid tag of each of the cell types of the unitary population of cells from the first sample and the exogenous nucleic acid tag of each of the cell types of the unitary population of cells from the second sample using pairs of primers that hybridize to the flanking amplification primer binding sequences, and quantifying each of the plurality of different amplified nucleic acid tags by hybridizing each of the plurality of different amplified nucleic acid tags with a plurality of different detectable oligonucleotides and quantifying an amount of each of the plurality of different detectable oligonucleotides bound to its corresponding amplified nucleic acid tag from the plurality of different amplified nucleic acid tags,
wherein at least one of the primers in each pair of the pairs of primers comprises a functional group for attachment to a detectably labeled bead having a reactive group that links to the functional group, wherein each of the plurality of different detectable oligonucleotides comprises a sequence specifically hybridizing to a core sequence that is unique to one of the cell types of the unitary population of cells and is present in one of the plurality of different amplified nucleic acid tags, wherein each of the plurality of different detectable oligonucleotides is attached to a detectably labeled bead comprising a label that is unique to one of the cell types of the unitary population of cells; and (e) simultaneously determining the effect of the test condition on viability or proliferation of the cells of each of the plurality of different genetically heterogeneous mammalian cell types by comparing the number of cells of each of the cell types of the unitary population of cells in the first sample after step c) to the number of cells of each of the same cell types of the unitary population of cells in the second sample after step c).

2. The method of claim 1, wherein the labeled bead is a fluorescent microsphere, and the method comprises detecting a fluorescence from the fluorescent microsphere.

3. The method of claim 2, further comprising simultaneously running another control sample in parallel with the unitary population of cells using the method of claim 1, wherein the control sample has no DNA template.

4. The method of claim 1, wherein said hybridizing each of the plurality of different amplified nucleic acid tags with a plurality of different detectable oligonucleotides is performed at 45° C.

5. The method of claim 1, wherein said hybridizing each of the plurality of different amplified nucleic acid tags with a plurality of different detectable oligonucleotides is performed for at least 6 or more hours.

6. The method of claim 1, further comprising producing lysed first sample and lysed second sample and heating the lysed first sample and the lysed second sample to 95° C. prior to the amplifying step.

7. The method of claim 1, wherein the plurality of different genetically heterogeneous cell types comprises cells from at least two different tissue types.

8. The method of claim 1, wherein the plurality of different genetically heterogeneous cell types comprises cells from at least two different tumor types.

9. The method of claim 1, wherein the unitary sample comprises five or more different genetically heterogeneous cell types.

10. The method of claim 1, wherein the period of time in step c) is 5 days.

* * * * *